(12) United States Patent
Wakana et al.

(10) Patent No.: US 12,303,155 B2
(45) Date of Patent: May 20, 2025

(54) SURGICAL TOOL, SURGERY SUPPORT SYSTEM, AND SURGICAL OPERATING UNIT

(71) Applicant: SONY GROUP CORPORATION, Tokyo (JP)

(72) Inventors: Kazuhito Wakana, Tokyo (JP); Kazuo Hongo, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 517 days.

(21) Appl. No.: 17/753,537

(22) PCT Filed: Aug. 31, 2020

(86) PCT No.: PCT/JP2020/032870
§ 371 (c)(1),
(2) Date: Mar. 7, 2022

(87) PCT Pub. No.: WO2021/049350
PCT Pub. Date: Mar. 18, 2021

(65) Prior Publication Data
US 2022/0330965 A1 Oct. 20, 2022

(30) Foreign Application Priority Data
Sep. 13, 2019 (JP) ................. 2019-166762

(51) Int. Cl.
*A61B 17/29* (2006.01)
*A61B 34/37* (2016.01)
(52) U.S. Cl.
CPC ...... *A61B 17/29* (2013.01); *A61B 2017/2903* (2013.01); *A61B 2017/2938* (2013.01);
(Continued)

(58) Field of Classification Search
CPC ......... A61B 17/29; A61B 34/35; A61B 34/37; A61B 34/71; A61B 2017/2938;
(Continued)

(56) References Cited

U.S. PATENT DOCUMENTS 6,411,519 B2 * 6/2002 Asai ................. H01L 23/49838
361/764
6,770,081 B1 8/2004 Cooper et al.
(Continued)

FOREIGN PATENT DOCUMENTS

CN 102171006 A 8/2011
JP 2002-503976 A 2/2002
(Continued)

OTHER PUBLICATIONS

International Search Report and Written Opinion of PCT Application No. PCT/JP2020/032870, issued on Nov. 10, 2020, 09 pages of ISRWO.

*Primary Examiner* — Jocelin C Tanner
(74) *Attorney, Agent, or Firm* — CHIP LAW GROUP

(57) ABSTRACT

A surgical tool having an open-close end effector is to be provided. The surgical tool includes: a shaft; a wrist that is connected to the shaft rotatably about a first axis; a first jaw member and a second jaw member, each of which is supported rotatably about a second axis; and an elastic member that applies a repulsive force between the first jaw member and the second jaw member. The surgical tool further includes: a first jaw capstan provided for the first jaw member; a first cable that pulls the first jaw member; a second jaw capstan provided for the second jaw member; and a second cable that pulls the second jaw member.

16 Claims, 19 Drawing Sheets

(52) U.S. Cl.
CPC . *A61B 2017/294* (2013.01); *A61B 2017/2947* (2013.01); *A61B 34/37* (2016.02)

(58) Field of Classification Search
CPC .... A61B 2017/2926; A61B 2017/2903; A61B 2017/294; A61B 2017/2947; A61B 2034/301; A61B 2034/302; A61B 2034/305; A61B 2034/715; B25J 17/0258; B25J 9/104; B25J 15/0233
USPC ........................................................ 606/206
See application file for complete search history.

(56) References Cited

U.S. PATENT DOCUMENTS

| | | |
|---|---|---|
| 2010/0011901 A1 | 1/2010 | Burbank |
| 2010/0082041 A1 | 4/2010 | Prisco |
| 2011/0301602 A1* | 12/2011 | Roy ................ A61B 17/29 606/205 |
| 2016/0113732 A1 | 4/2016 | Steege et al. |
| 2022/0071726 A1* | 3/2022 | Rockrohr ............. A61B 34/30 |

FOREIGN PATENT DOCUMENTS

| | | |
|---|---|---|
| JP | 2012-504016 A | 2/2012 |
| JP | 2018-534100 A | 11/2018 |
| JP | 2019-501699 A | 1/2019 |
| JP | 2019-034002 A | 3/2019 |
| KR | 10-2011-0069114 A | 6/2011 |
| WO | 2010/009221 A2 | 1/2010 |
| WO | 2010/039387 A1 | 4/2010 |
| WO | 2014/201010 A1 | 12/2014 |

* cited by examiner

SURGICAL TOOL, SURGERY SUPPORT SYSTEM, AND SURGICAL OPERATING UNIT

CROSS REFERENCE TO RELATED APPLICATIONS

This application is a U.S. National Phase of International Patent Application No. PCT/JP2020/032870 filed on Aug. 31, 2020, which claims priority benefit of Japanese Patent Application No. JP 2019-166762 filed in the Japan Patent Office on Sep. 13, 2019. Each of the above-referenced applications is hereby incorporated herein by reference in its entirety.

TECHNICAL FIELD

The technology disclosed in this specification (hereinafter referred to as "the present disclosure") relates to a surgical tool to be used in a surgery support system, for example, a surgery support system, and a surgical operating unit.

BACKGROUND ART

Advances in the robotics technologies in recent years are remarkable, and robots are now widely used in work sites in various industrial fields. For example, in the field medicine, a master-slave surgical robot is becoming widespread. This kind of surgical robot is designed so that an operator such as a surgeon operates, from the master side, one or a plurality of surgical tools included in a slave device. Also, as a known method for controlling a master-slave system, there is a bilateral method by which a slave device is operated from a master device, and at the same time, the state of the slave device is fed back to the master device (see Patent Document 1, for example). An end effector having an opening and closing mechanism such as forceps is provided at the end of a surgical tool mounted in a slave device. Further, on the assumption that a surgical tool is to be used in an operation in a body cavity, on a body surface, or the like, the end of a surgical tool is strongly desired to have multiple degrees of freedom, have a small diameter, be small in size, and be light in weight. Specifically, the end of a surgical tool is desired to have a total of three degrees of freedom, which are two degrees of freedom of rotation and a degree of freedom of opening and closing. Further, for miniaturization of surgical tools, a drive method using a cable is often adopted in handling the end of a surgical tool (see Patent Documents 2 to 4, for example).

CITATION LIST

Patent Documents

Patent Document 1: Japanese Patent Application Laid-Open No. 2019-34002
Patent Document 2: Japanese Patent Application Laid-Open No. 09-542671
Patent Document 3: JP 2018-534100 W
Patent Document 4: JP 2019-501699 W

SUMMARY OF THE INVENTION

Problems to be Solved by the Invention

An object of the technology according to the present disclosure is to provide a surgical tool that has an open-close end effector such as forceps at its end, is designed to be small in size and light in weight, and is used in a surgery support system, and to provide a surgery support system and a surgical operating unit.

Solutions to Problems

A first aspect of the technology according to the present disclosure is
a surgical tool that includes:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

The surgical tool according to the first aspect further includes: a first jaw capstan that is provided for the first jaw member, and uses the second axis as its rotation axis; a first cable that is wound around the first jaw capstan; a second jaw capstan that is provided for the second jaw member, and uses the second axis as its rotation axis; and a second cable that is wound around the second jaw capstan. Further, the first jaw member turns in a direction toward the second jaw member by pulling the first cable, and the second jaw member turns in a direction toward the first jaw member by pulling the second cable.

The surgical tool according to the first aspect further includes: a wrist capstan that is provided for the wrist, and uses the first axis as its rotation axis; a third cable that includes forward and backward cables wound around the wrist capstan from opposite directions; a first actuator that pulls the first cable; a second actuator that pulls the second cable; and a third actuator that pulls the third cable.

Further, a second aspect of the technology according to the present disclosure is
a surgery support system that includes a surgical tool, and an arm to which the surgical tool is attached,
the surgical tool including:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

Further, a third aspect of the technology according to the present disclosure is
a surgical operating unit that includes a surgical tool, and a handle unit to which the surgical tool is attached,
the surgical tool including:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

Effects of the Invention

By the technology according to the present disclosure, it is possible to provide a surgical tool that has an open-close end effector such as forceps at its end, includes a smaller number of components, has a smaller diameter, and is used in a surgery support system, and to provide a surgery support system and a surgical operating unit.

Note that the advantageous effects described in this specification are merely examples, and the advantageous effects to be brought about by the technology according to the present disclosure are not limited to them. Furthermore, in some cases, the technology according to the present disclosure may exhibit additional advantageous effects, in addition to the above advantageous effects.

Other objects, features, and advantages of the technology according to the present disclosure will be made apparent by the embodiments described below and the detailed descriptions with reference to the accompanying drawings.

MODE FOR CARRYING OUT THE INVENTION

Figure 1:
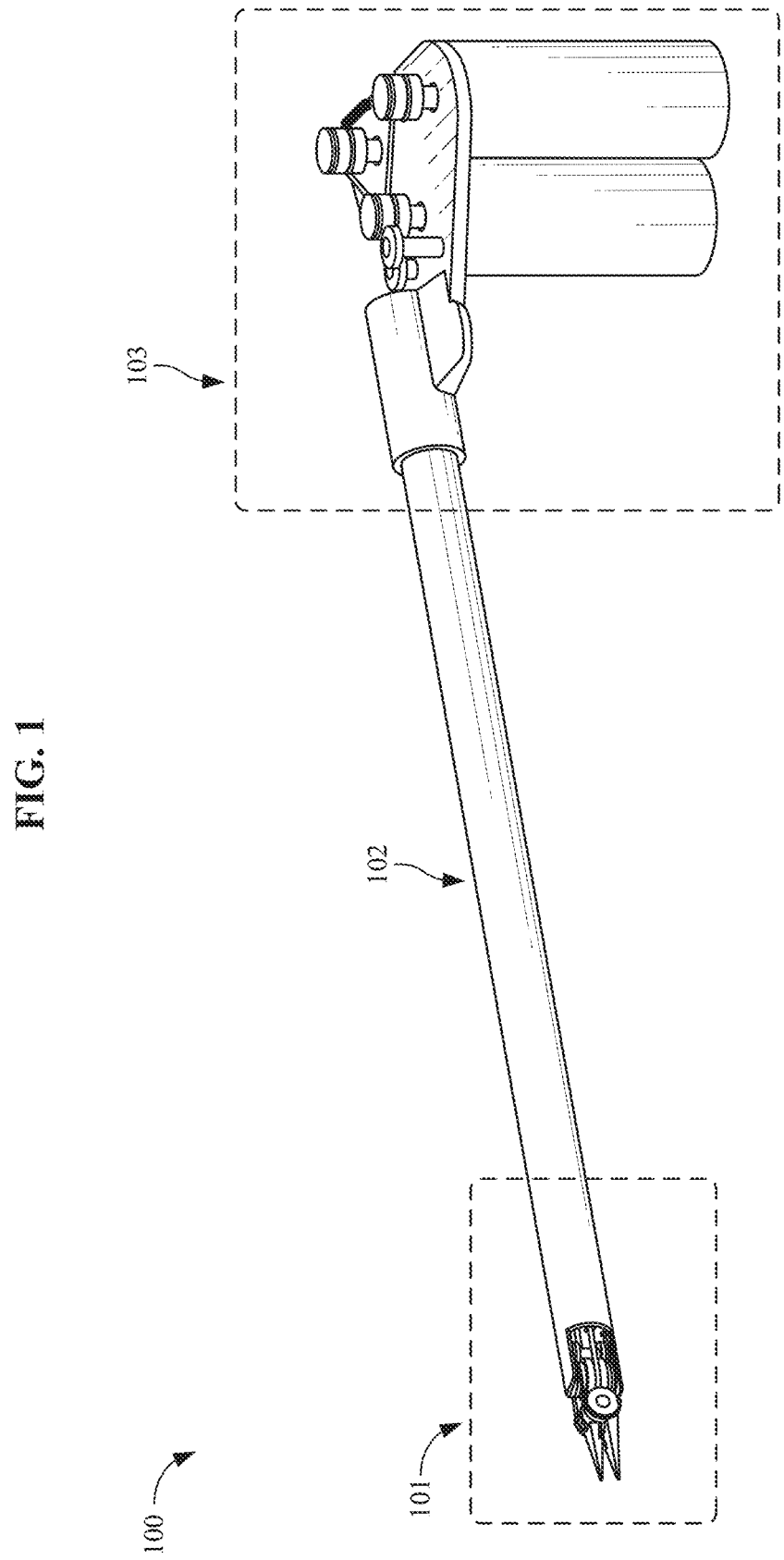
FIG. 1 is a diagram showing an example configuration of a surgical tool unit 100.

In the description below, the technology according to the present disclosure will be explained in the following order, with reference to the drawings.

A. Problems with a Surgical Tool Unit
B. Example Configuration of a Surgical Tool Unit
C. Operations of a Surgical Tool Unit
D. Range of Movement of a Surgical Tool Unit
E. Modifications of the Surgical Tool Unit
F. Example Applications of the Surgical Tool Unit
G. Effects A. Problems with a Surgical Tool Unit A surgical tool to be used in a surgery support system preferably has a total of three degrees of freedom, which are two degrees of freedom of rotation and a degree of freedom of opening and closing at the end. Specifically, such a surgical tool includes an open-close end effector formed with a pair of opposing jaw members, a wrist supporting the end effector, and a shaft that has a longitudinal axis and connects the wrist to its end, for example. This kind of surgical tool has a degree-of-freedom configuration including: a first axis for turning the wrist about the yaw axis, for example, with respect to the end of the shaft; a second axis for turning the orientation of the end effector about the pitch axis, for example, with respect to the wrist; and a third axis (an open-close shaft) for opening and closing the jaw members. In the description below, an embodiment in which the second axis and the open-close shaft are coaxial will be described.

In laparoscopic surgery, for example, the end (distal end) side of the shaft is normally used while inserted in a body cavity via a trocar, and therefore, needs to have a small diameter. Further, in brain surgery, treatment needs to be performed on a narrow operative field, and therefore, it is necessary to minimize hindering of the field of view of the operator, depending on the surgical tool. In view of this, the driving forces generated by actuators (electromagnetic rotary motors, for example) disposed on the root side (the proximal end) of the shaft are basically transmitted via cables, so as to operate the surgical tool. Specifically, three systems of cables for transmitting the power for turning the wrist about the first axis with respect to the shaft end, the power for turning the monitoring orientation about the second axis with respect to the wrist, and the power for opening and closing the open-close end effector are required, and these cables are inserted through the shaft. Further, in a power transmission mechanism using cables, a plurality of pulleys is used, such as capstans for applying power to the cables or converting the forces from the cables into axial forces, and idler pulleys to be used for adjusting the layout of the cables in the shaft and applying constant tension to the cables.

Here, according to a method by which the layout of cables is adjusted with idler pulleys, high slidability is achieved. Thus, excellent durability and reliability are also achieved, and torque control on the end effector can be performed with high precision. On the other hand, the number of components increases by the number of idler pulleys. Therefore, the surgical tool (or the outer diameter of the shaft, for example) becomes larger in size, and the costs become higher. According to a method by which the cables are made to slide on an R surface formed on a peripheral component without the use of any idler pulley, it is possible to reduce the number of components and achieve a smaller size by eliminating the idler pulleys. However, the cables easily deteriorate due to abrasion, and the reliability becomes poorer. Furthermore, the friction coefficient on the sliding surface is high, which leads to disturbance. As a result, torque control becomes difficult. It is also possible to adopt a method by which cables are inserted through a round hole formed along a desired layout. However, backlash occurs when the cables inserted through the round hole are handled.

Also, a cable loop type or an individual cable traction type can be normally adopted as a method for driving a capstan on the output side with a cable tractive force generated by an actuator.

In the former cable loop type, the cables are laid out by looping the output-side capstan and the drive-side capstan that is rotated by drive of an actuator. With the cable loop type, the forward and backward cables can be controlled in an antagonistic manner by a single actuator, it is easy to make the drive unit smaller in size and lighter in weight. Furthermore, there is no need to compensate the pre-tension of the cables with an output of the actuator, and thus, the actuator can be easily made smaller in size. However, in the case of a device configuration in which the entire length of the looped cables fluctuates due to the influence of the axis angle of the control target and other axes, the pre-tension to be applied to the cables fluctuates, and therefore, it is difficult to adopt the cable loop type. For example, when the wrist is driven to rotate about the first axis, the lengths of the respective cable for driving the respective jaw members change.

On the other hand, the latter individual cable traction type has a configuration in which the forward and backward cables attached to the capstans on the output side are pulled by individual actuators, and the forward and backward cables can be controlled independently of each other. Thus, the degree of freedom in designing the configuration of a surgical tool becomes higher. However, the pre-tension of the cables needs to be compensated with outputs of the actuators. Although it is also possible to compensate the pre-tension using a coil spring, a weight, or the like, control becomes difficult because the corresponding spring force or inertial force is applied when driving is performed with the actuators.

In both the cable loop type and the individual cable traction type, one traction motor is required for each one cable. If heavy and large motors for compensating the pre-tension of the cables are installed as many as the number of cables, the housing space and the device weight increase. Also, in both the cable loop type and the individual cable traction type, a total of two cables that are forward and backward cables are used for bidirectionally rotating one output-side capstan. Therefore, two idler pulleys for adjusting the layout of the cables are also required, and the number of components increases.

In view of the above, this specification discloses below a surgical tool that achieves size and weight reduction by adjusting the layout of cables with a smaller number of idler pulleys, and pulling the cables by a method that facilitates application of desired pre-tension. This specification also discloses below a surgery support system and a surgical operating unit.

B. Example Configuration of a Surgical Tool Unit

FIG. 1 shows an example configuration of a surgical tool unit 100 to which the technology according to the present disclosure is applied. The surgical tool unit 100 includes a hollow shaft 102 having a longitudinal axis, a surgical tool unit end portion 101 at one end of the shaft 102, and a surgical tool unit drive unit 103 at the other end of the shaft 102. As will be described later, the surgical tool unit end portion 101 includes a wrist element capable of turning about a first axis parallel to the yaw axis with respect to the shaft 102, and an end effector at the end of the wrist element. The end effector performs an opening and closing operation with a second axis functioning as the open-close shaft, the second axis being parallel to the pitch axis. The end effector is formed with a pair of opposing jaw members that turn about the second axis and perform an opening and closing operation. Meanwhile, the surgical tool unit drive unit 103 includes one actuator that drives the wrist of the surgical tool unit end portion 101, two actuators that drive the respective jaw member, and a base member that attaches these actuators to a portion near the other end of the shaft 102. However, the second axis is located at a position offset from the first axis.

Figure 2:
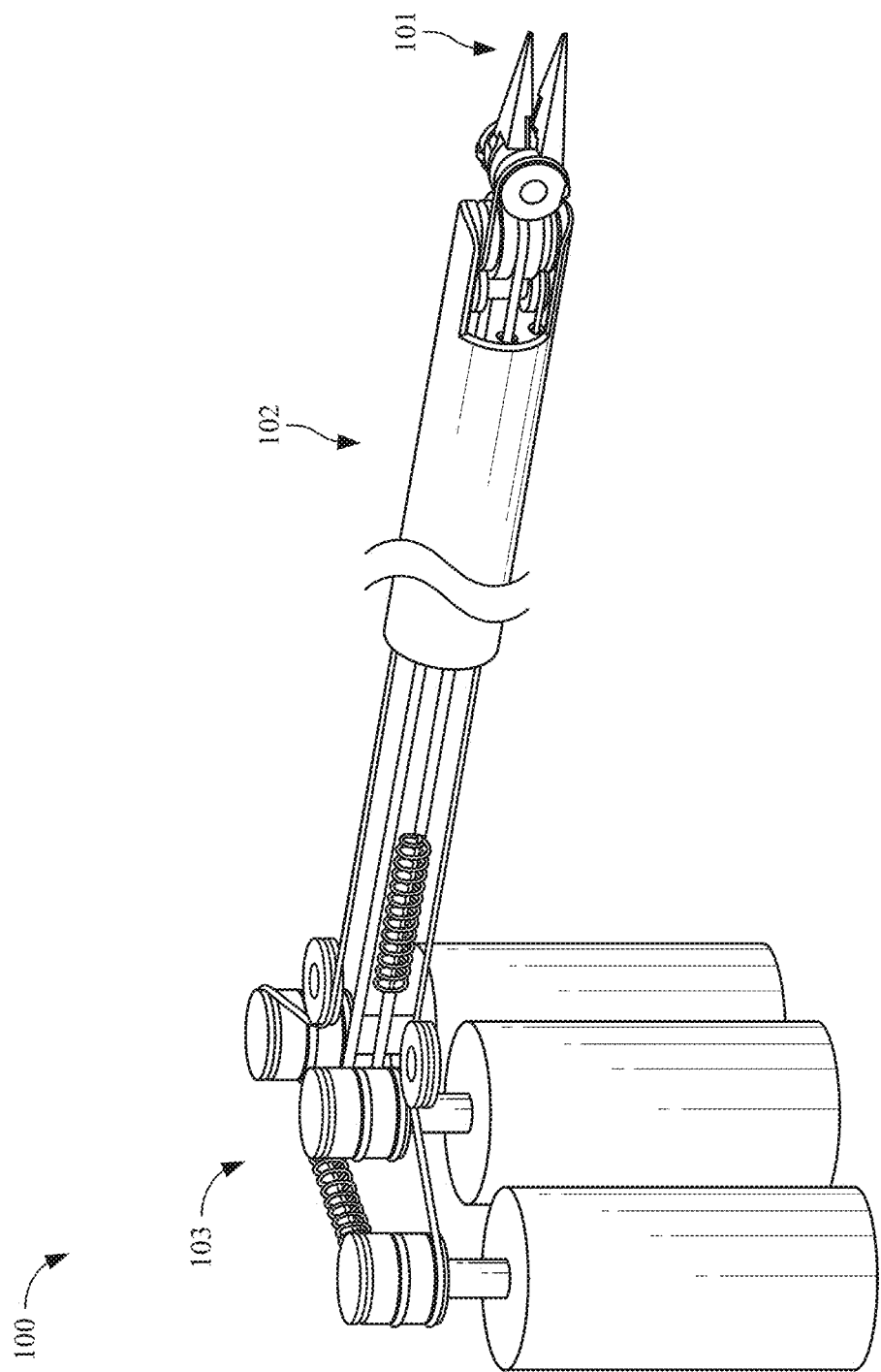
FIG. 2 is an enlarged view of each relevant part of a surgical tool unit end portion 101 and a surgical tool unit drive unit 103 of the surgical tool unit 100.
Figure 3:
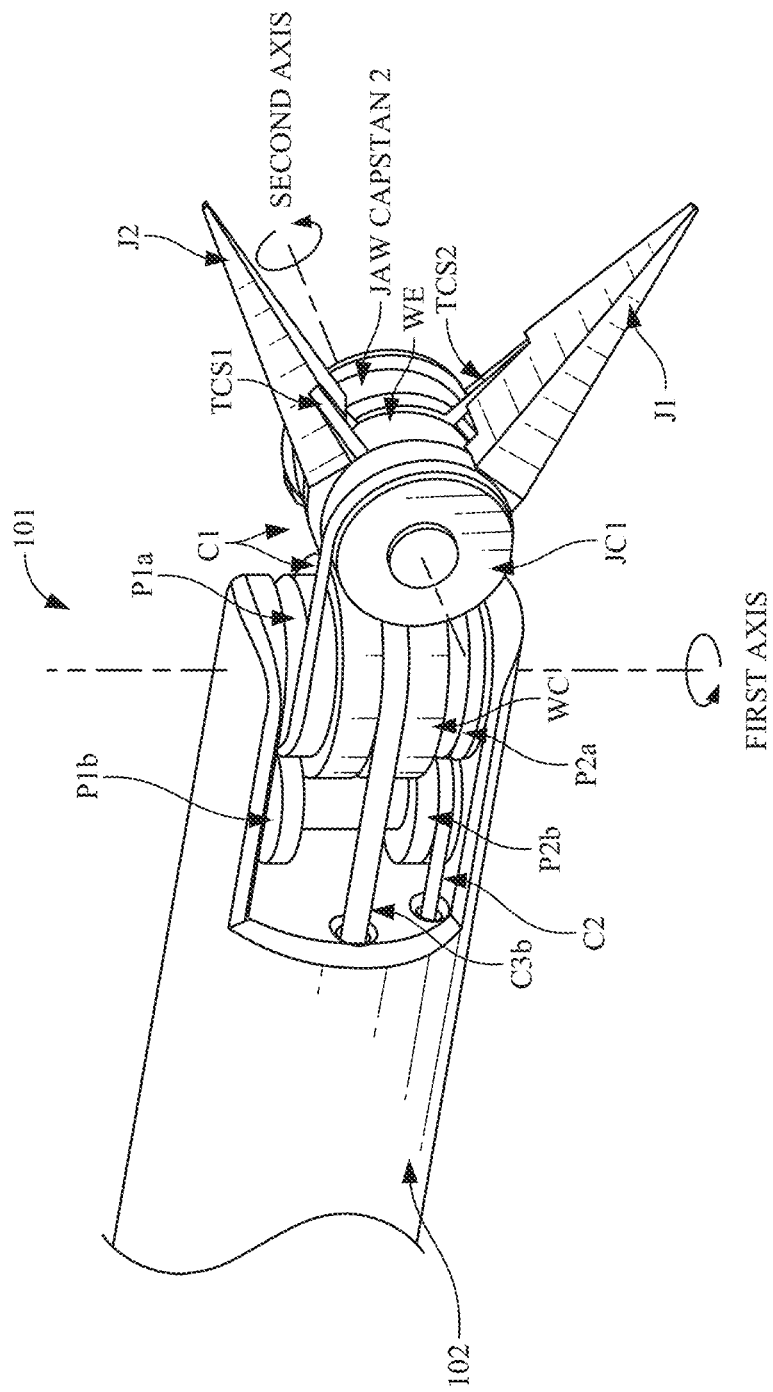
FIG. 3 is an enlarged view of the surgical tool unit end portion 101.
Figure 4:
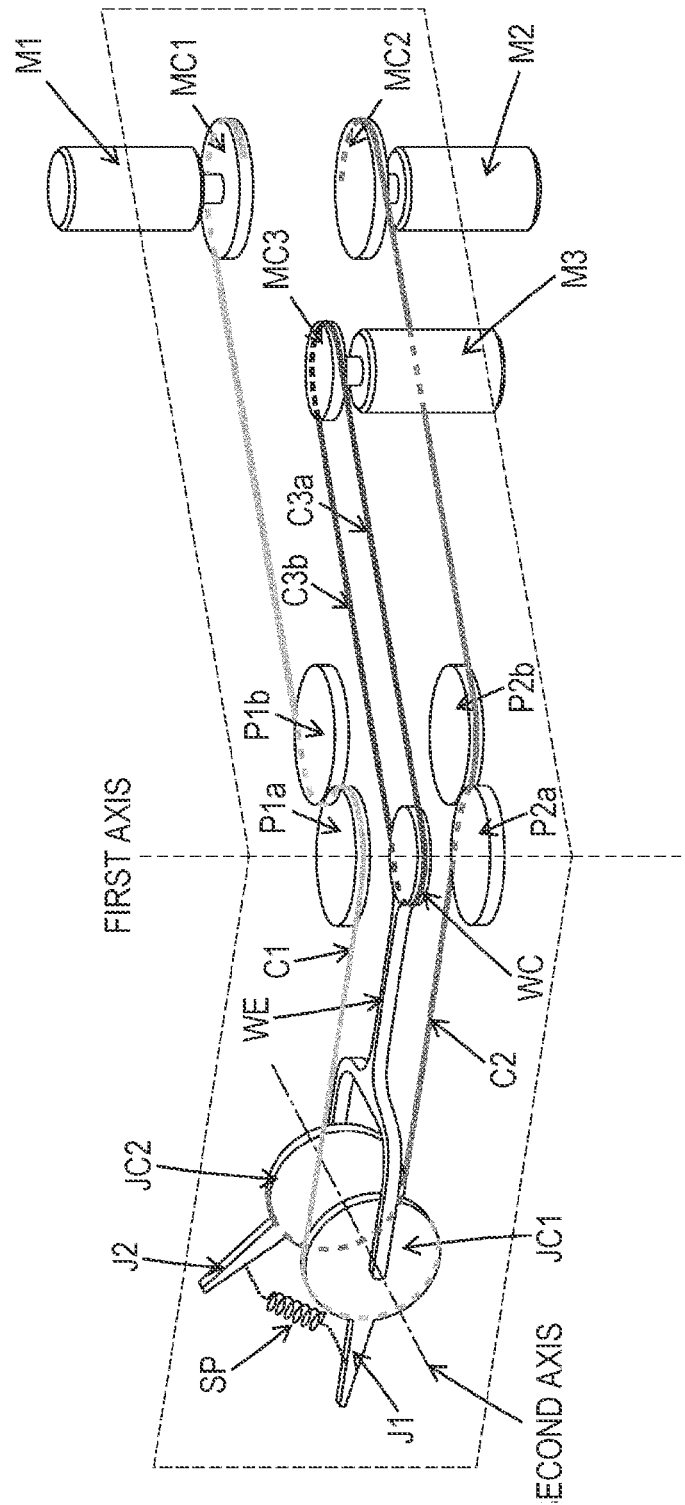
FIG. 4 is a diagram showing an example degree-of-freedom configuration of the surgical tool unit 100.
Figure 5:
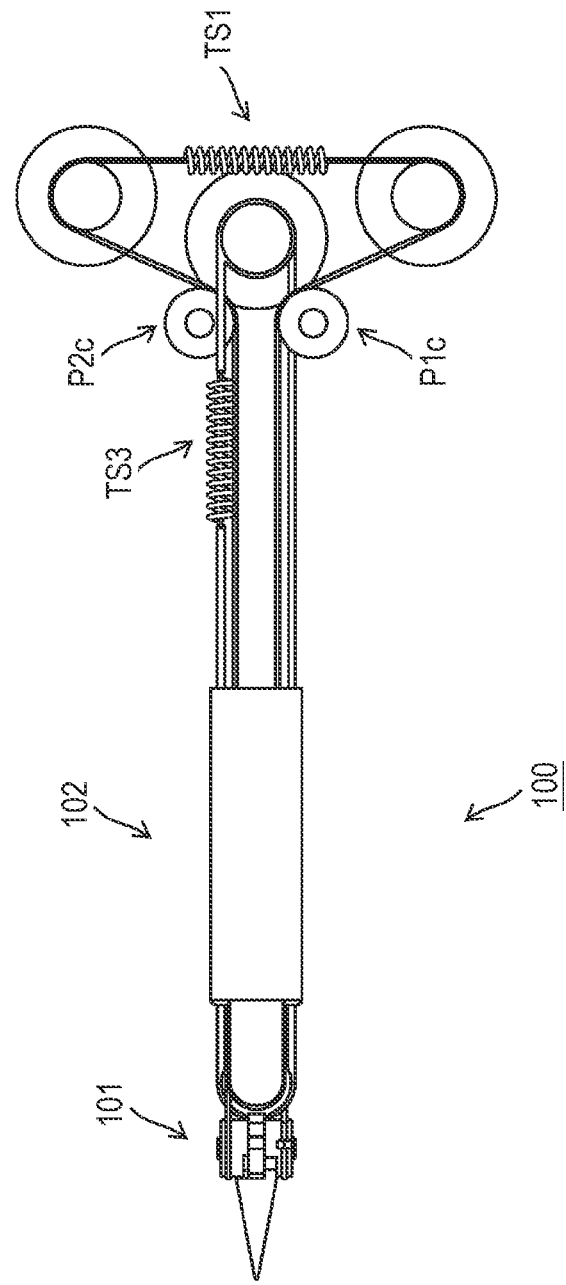
FIG. 5 is a diagram showing the surgical tool unit 100 as viewed from above.

In FIG. 2, each relevant part of the surgical tool unit end portion 101 and the surgical tool unit drive unit 103 of the surgical tool unit 100 are shown in an enlarged manner. Also, FIG. 3 shows the surgical tool unit end portion 101 in an enlarged manner. Further, FIG. 4 shows an example degree-of-freedom configuration of the surgical tool unit 100. Furthermore, FIG. 5 shows the surgical tool unit 100 as viewed from above.

The surgical tool unit end portion 101 includes a wrist element WE and an open-close end effector. The end effector includes a pair of opposing jaw members: a first jaw member J1 and a second jaw member J2 (see FIG. 3, for example). The wrist element WE is supported at a portion near the root so as to be able to turn about the first axis parallel to the yaw axis at the end (distal end) of the shaft 102. Further, the first jaw member J1 and the second jaw member J2 that constitute the end effector are supported so as to be able to turn about the second axis parallel to the pitch axis at the end of the wrist element WE. The first jaw member J1 and the second jaw member J2 open and close when the open angle changes, with the second axis serving as the open-close shaft.

Meanwhile, the surgical tool unit drive unit 103 includes a first motor M1 to be used for driving the first jaw member J1, a second motor M2 to be used for driving the second jaw member J2, and a motor M3 to be used for driving the wrist element WE (see FIG. 2, for example). Further, motor capstans MC1, MC2, and MC3 as drive capstans are attached to the output shafts of these motors M1 to M3, respectively (see FIG. 4, for example). These motors M1 to M3 are then supported at an end (the proximal end) of the shaft 102 by the base member. Although a rotary motor is assumed to be used for each of the motors M1 to M3 in this embodiment, a motor with a speed reducer may also be used.

In the vicinity of the base of the wrist element WE, a wrist capstan WC using the first axis as its rotation axis is provided. Further, a third cable inserted through the shaft 102 is wound around the wrist capstan WC and the third motor capstan MC3. The driving force generated by the third motor M3 is then transmitted by the third cable, and a turning operation of the wrist element WE about the first axis is performed.

In the example shown in FIG. 4, the third cable is formed with a forward cable C3a and a backward cable C3b, and has a cable loop type configuration in which the third motor capstan MC3 on the drive side and the wrist capstan WC on the output side are looped. When the third motor M3 is rotated, a difference in tension is generated between the forward cable C3a and the backward cable C3b, depending on the rotation direction. Therefore, the rotation torque based on the tension difference acts on the wrist capstan WC, and the wrist element WE turns about the first axis. Accordingly, the third motor M3 controls the forward cable C3a and the backward cable C3b in an antagonistic manner, so that the wrist element WE can be made to turn about the first axis.

Further, to prevent bending, a tension spring TS3 that provides pre-tension is inserted into the third cable formed with the cable C3a and the cable C3b. In the example shown in FIGS. 4 and 5, the tension spring TS3 is inserted at the side of the cable C3b. Alternatively, pre-tension may be provided by an additional idler pulley.

Note that the third cable may not be of a loop type, and the forward cable C3a and the backward cable C3b may be pulled by different motors independently of each other so as to turn the wrist element WE about the first axis. However, the number of motors will increase.

The first jaw member J1 is supported by the wrist element WE near the root so as to be able to turn about the second axis (see FIGS. 3 and 4, for example). Likewise, the second jaw member J2 is supported by the wrist element WE near the root so as to be able to turn about the second axis (see FIGS. 3 and 4, for example). Accordingly, each of the first jaw member J1 and the second jaw member J2 is turned about the second axis, so that the open angle of the first jaw member J1 and the second jaw member J2 become larger or smaller (in other words, so that a change is caused in the difference between the angles of the first jaw member J1 and the second jaw member J2 about the second axis). Thus, an opening and closing operation of the end effector is performed. Further, the first jaw member J1 and the second jaw member J2 are simultaneously turned about the second axis, while the open angle of the first jaw member J1 and the second jaw member J2 are maintained at constant angles (in other words, to cause a change in the sum of the angles of the first jaw member J1 and the second jaw member J2 about the second axis). Thus, a turning operation of the end effector formed with the first jaw member J1 and the second jaw member J2 about the second axis is performed.

A first jaw capstan JC1 having the above-mentioned second axis as its rotation axis is provided near the root of the first jaw member J1. A first cable C1 is then wound around the first jaw capstan JC1 and the first motor capstan MC1, so that the driving force generated by the first motor M1 is transmitted by the first cable C1, and a turning operation of the first jaw member J1 about the second axis is performed (see FIG. 4, for example). As the connected portion between the first jaw capstan JC1 and the first cable C1 can be set at any position on the outer periphery of the first jaw capstan JC1, the range of movement of the first jaw member J1 can be made wider.

Also, a second jaw capstan JC2 having the above-mentioned second axis as its rotation axis is provided near the root of the second jaw member J2. A second cable C2 is then wound around the second jaw capstan JC2 and the second motor capstan MC2, so that the driving force generated by the second motor M2 is transmitted by the second cable C2, and a turning operation of the second jaw member J2 about the second axis is performed (see FIG. 4, for example). As the connected portion between the second jaw capstan JC2 and the second cable C2 can be set at any position on the outer periphery of the second jaw capstan JC2, the range of movement of the second jaw member J2 can be made wider.

Here, the first cable C1 and the second cable C2 are wound around the first jaw capstan JC1 and the second jaw capstan JC2, respectively, from opposite directions. Specifically, the first cable C1 is wound around the first jaw capstan JC1 so that the first jaw member J1 turns in a direction to approach the second jaw member J2 when the first cable C1 is pulled. Also, the second cable C2 is wound around the second jaw capstan JC2 so that the second jaw member J2 turns in a direction to approach the first jaw member J1 when the second cable C2 is pulled. Accordingly, the tractive force of the first cable C1 and the second cable C2 is controlled by the first motor M1 and the second motor M2 so that a change is caused in the difference between the angles of the first jaw member J1 and the second jaw member J2 about the second axis. Thus, an opening and closing operation of the end effector formed with the first jaw member J1 and the second jaw member J2 can be performed. Also, the tractive force of the first cable C1 and the second cable C2 is controlled by the first motor M1 and the second motor M2 so that a change is caused in the sum of the angles of the first jaw member J1 and the second jaw member J2 about the second axis. Thus, the end effector formed with the first jaw member J1 and the second jaw member J2 can be made to turn about the second axis.

Figure 6:
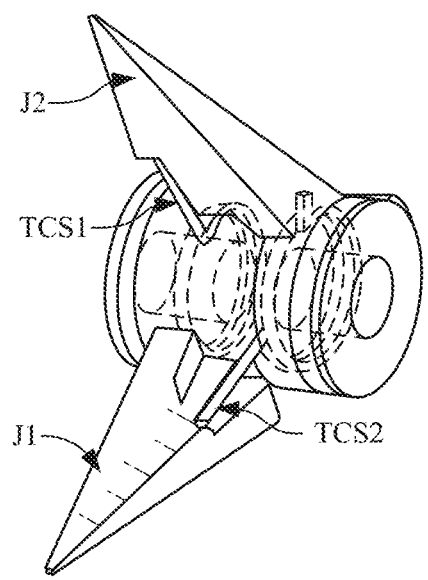
FIG. 6 is an enlarged view of the surgical tool unit end portion 101.
Figure 7:
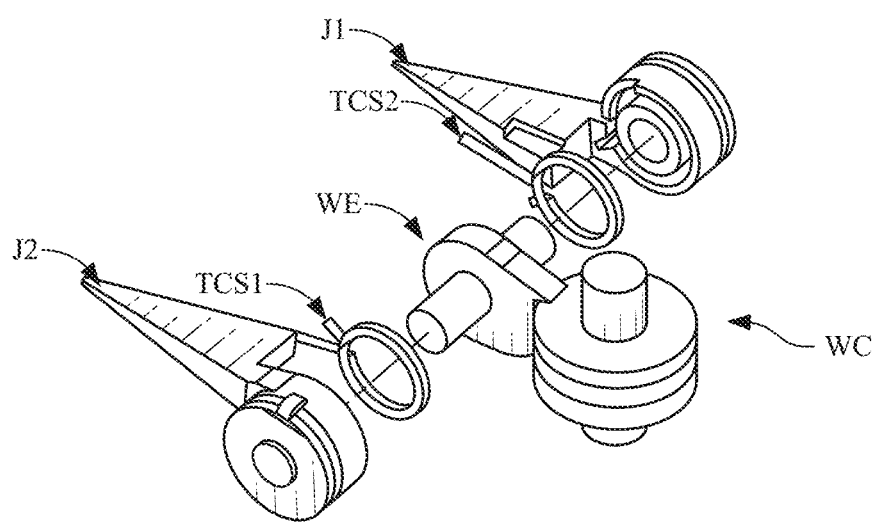
FIG. 7 is a diagram showing a component development view of the surgical tool unit end portion 101.

A spring SP is disposed between the first jaw member J1 and the second jaw member J2 so that a repulsive force always acts in the opening direction (see FIG. 4, for example). FIG. 6 shows an example of installation of the spring SP in an enlarged view of the surgical tool unit end portion 101. Further, FIG. 7 shows a component development view of the surgical tool unit end portion 101 shown in FIG. 6. In the example shown in FIGS. 6 and 7, the spring SP shown in FIG. 4 is formed with a first torsion coil spring TCS1 that is attached to the second axis at the end of the wrist element WE and applies a rotative force to the first jaw member J1 in the direction of opening from the second jaw member J2, and a second torsion coil spring TCS2 that applies a rotative force to the second jaw member J2 in the direction of opening from the first jaw member J1. A torsion coil spring is a coil spring that applies a torsional moment about the coil central axis. Accordingly, pre-tension always acts on the first jaw member J1 and the second jaw member J2 in the opening direction.

The first torsion coil spring TCS1 is in contact only with the first jaw member J1, and not with the wrist element WE. Likewise, the second torsion coil spring TCS2 is in contact only with the second jaw member J2, and not with the wrist element WE. Accordingly, even if the angle of the end effector about the first axis is changed while the open angle between the first jaw member J1 and the second jaw member J2 is kept constant, a constant repulsive force can be applied between the first jaw member J1 and the second jaw member J2.

As shown in FIGS. 6 and 7, torsion coil springs are preferably used for the spring SP. Note that, in the example shown in FIGS. 6 and 7, two torsion coil springs are used, but the number of springs to be used for generating a repulsive force is not limited to any particular number. Further, instead of springs, magnets or the like may be used to generate a repulsive force (for example, a repulsive force between magnets of the same polarity is used).

As described above, a repulsive force acts between the first jaw member J1 and the second jaw member J2 because of the restoring force of the spring SP (or the first torsion coil spring TCS1 and the second torsion coil spring TCS2), and pre-tension constantly acts in the opening direction. Accordingly, when the first jaw member J1 is pulled in the closing direction by the first motor M1 using a single first cable C1 (in other words, only a forward first cable), and the second jaw member J2 is pulled in the closing direction by the second motor M2 using a single second cable C2 (in other words, only a forward second cable), the first jaw member J1 and the second jaw member J2 can be closed. Also, when the traction by the first motor M1 and the second motor M2 is stopped, the first jaw member J1 and the second jaw member J2 spontaneously open because of the restoring force of the spring SP (or the first torsion coil spring TCS1 and the second torsion coil spring TCS2). That is, since an operation of opening the first jaw member J1 and the second jaw member J2 is performed with the elastic force of the torsion coil springs TCS1 and TCS2, backward cables for opening the jaw members are not necessary.

Accordingly, one cable that pulls in the closing direction is used for each jaw member, and the tension of the cables and the repulsive force of the elastic members are controlled in an antagonistic manner by a single actuator disposed at the input end of each cable, so that the jaw members can be opened and closed. That is, the number of cables and the number of actuators necessary for opening and closing the jaw members can be reduced.

Note that the spring SP has a natural length in which a repulsive force acts even at the maximum open angle of the first jaw member J1 and the second jaw member J2. Alternatively, with the first torsion coil spring TCS1 and the second torsion coil spring TCS2, a repulsive force acts even at the maximum open angle of the first jaw member J1 and the second jaw member J2.

Idler pulleys are used to redirect each of the first cable C1 and the second cable C2 at a portion near the first axis so that each of the cables is inserted through the shaft 102, and to adjust the layout of the respective cables in the shaft 102. As described above, it should be understood that, because the cables for pulling each of the first jaw member J1 and the second jaw member J2 are reduced to only one forward cable, the number of necessary idler pulleys is also reduced, leading to cost reduction.

In the example shown in FIGS. 3 and 4, the first cable C1 attached to the first jaw capstan JC1 is pulled in a direction orthogonal to the second axis, but is switched to a direction orthogonal to the first axis by a first idler pulley P1*a* that uses the first axis as its rotation axis. Further, by a first adjacent idler pulley P1*b* that is adjacent to the first idler pulley P1*a* and has a rotation axis parallel to the first axis, the first cable C1 is inserted through the shaft 102, is switched to the longitudinal axis direction of the shaft 102, and is then wound around the first motor capstan MC1 at the other end.

The first cable C1 is wound from the direction in which the distance to the first idler pulley P1*a* is shortest. Also, the first cable C1 is wound so that the first idler pulley P1*a* and the first adjacent idler pulley P1*b* rotate in opposite directions when pulling the first cable C1. Further, when the first motor capstan MC1 is rotated by the first motor M1 to generate the tractive force for the first cable C1, torque about the second axis is applied to the first jaw member J1, so that the first jaw member J1 can be turned in a direction to approach the second jaw member J2 (the closing direction).

Also, in the example shown in FIGS. 3 and 4, the second cable C2 attached to the second jaw capstan JC2 is pulled in a direction orthogonal to the second axis, but is switched to a direction orthogonal to the first axis by a second idler pulley P2*a* that uses the first axis as its rotation axis. Further, by a second adjacent idler pulley P2*b* that is adjacent to the second idler pulley P2*a* and has a rotation axis parallel to the first axis, the second cable C2 is inserted through the shaft 102, is switched to the longitudinal axis direction of the shaft 102, and is then wound around the second motor capstan MC2 at the other end.

The second cable C2 is wound from the direction in which the distance to the second idler pulley P2*a* is shortest. Also, the second cable C2 is wound so that the second idler pulley P2*a* and the second adjacent idler pulley P2*b* rotate in opposite directions when pulling the second cable C2. Here, the direction in which the second cable C2 is wound around the second idler pulley P2*a* is the opposite direction to the direction in which the first cable C1 is wound around the first idler pulley P1*a*. Further, when the second motor capstan MC2 is rotated by the second motor M2 to generate the tractive force for the second cable C2, torque about the second axis is applied to the second jaw member J2, so that the second jaw member J2 can be turned in a direction to approach the first jaw member J1 (the closing direction).

To be more specific, the orientation of the second cable C2 wound around the second jaw capstan JC2 is switched to the longitudinal axis direction of the shaft 102 through a path that is point symmetrical to the first cable C1, with respect to the second idler pulley P2*a* and the second adjacent idler pulley P2*b*. Further, the first idler pulley Pa1 and the second idler pulley P2*a* preferably have the same diameter. The first adjacent idler pulley P1*b* and the second adjacent idler pulley P2*b* do not necessarily have the same diameter as the first idler pulley Pa1 and the second idler pulley P2a, but are preferably of an appropriate size for allowing each of the first cable C1 and the second cable C2 to pass through the inside of the shaft 102.

Figure 8:
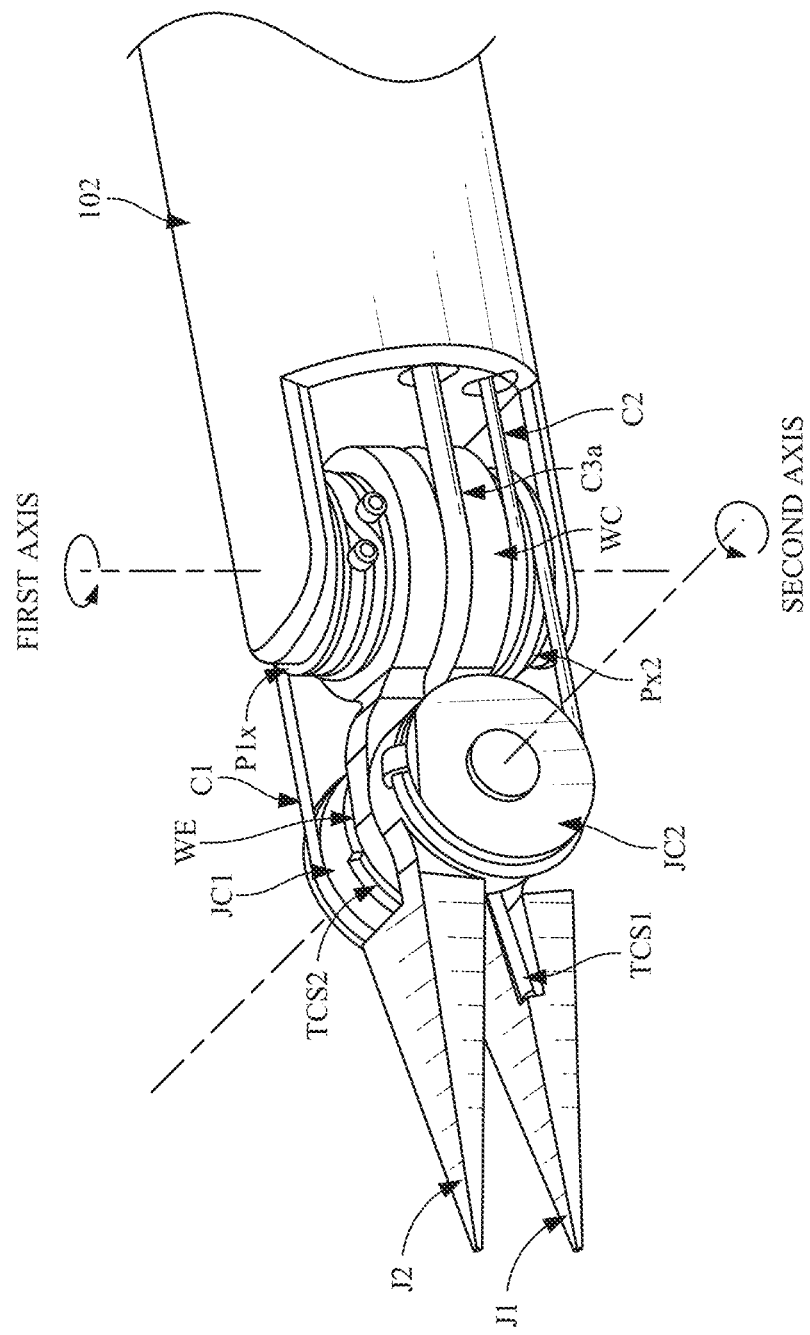
FIG. 8 is a diagram showing another example configuration of the surgical tool unit end portion 101.
Figure 9:
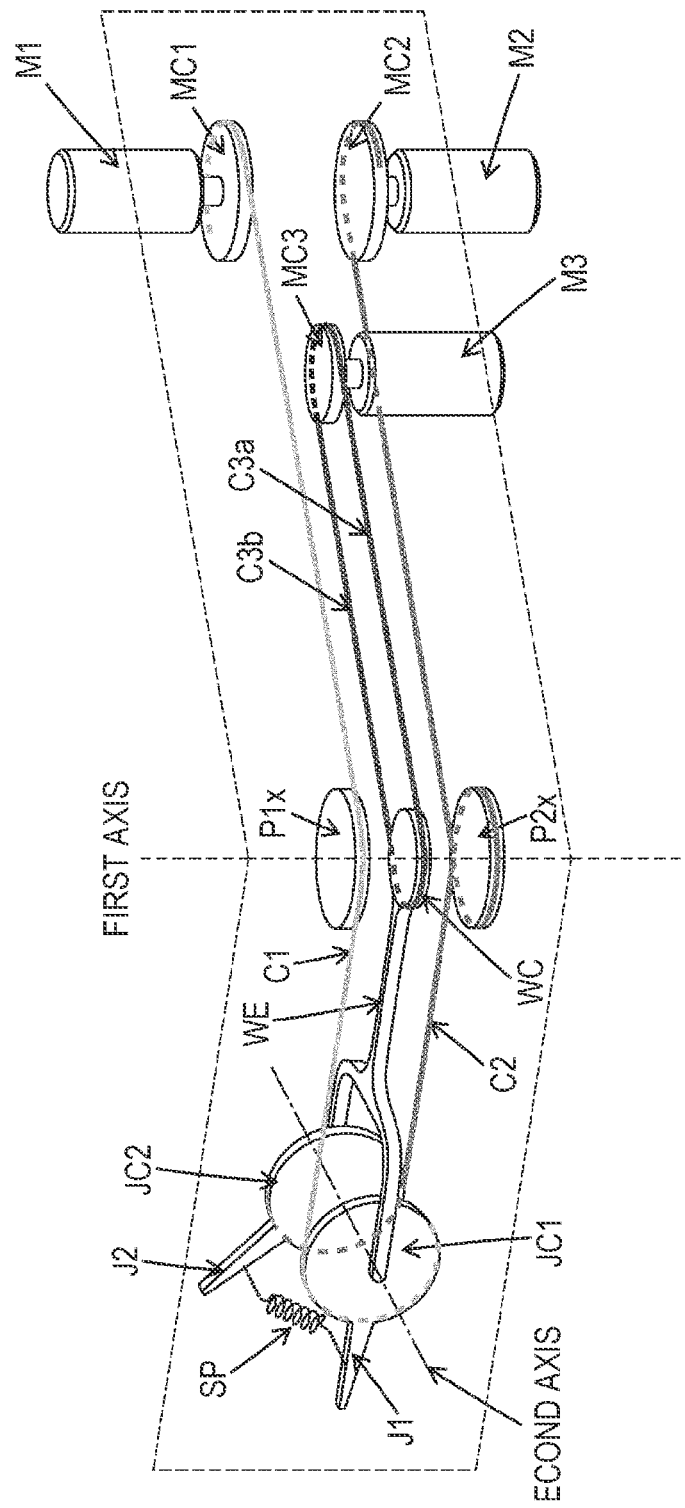
FIG. 9 is a diagram showing another example degree-of-freedom configuration of the surgical tool unit 100.

Further, FIG. 8 shows another example configuration of the surgical tool unit end portion 101. FIG. 9 shows another example degree-of-freedom configuration of the surgical tool unit 100 in a case where the surgical tool unit end portion 101 has the configuration shown in FIG. 8. The example configuration shown in FIGS. 8 and 9 differs from the example degree-of-freedom configuration shown in FIGS. 3 and 4 in the configuration of the idler pulleys that are used for the respective cables of the first cable C1 and the second cable C2.

In the example shown in FIGS. 8 and 9, the first cable C1 attached to the first jaw capstan JC1 is pulled in a direction orthogonal to the second axis. However, as the first cable C1 is wound at least once around a first idler pulley P1x that uses the first axis as its rotation axis, the first cable C1 is inserted through the shaft 102 and is switched to the direction so as to be pulled in the longitudinal axis direction of the shaft 102, and is then wound around the first motor capstan MC1 at the other end. The first cable C1 is wound from the direction in which the distance to the first idler pulley P1x is shortest. Further, when the first motor capstan MC1 is rotated by the first motor M1 to generate the tractive force for the first cable C1, torque about the second axis is applied to the first jaw member J1, so that the first jaw member J1 can be turned in a direction to approach the second jaw member J2 (the closing direction).

Figure 10:
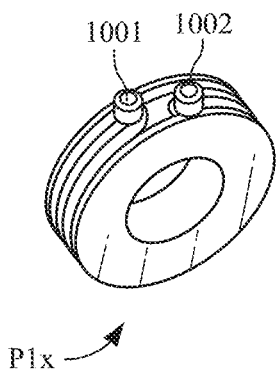
FIG. 10 is a diagram showing an example configuration of a first idler pulley P1x including a switching unit.

Note that a switching unit that switches the winding position in the first axis direction is disposed at a portion on the outer periphery of the first idler pulley P1x so that the cables do not overlap each other when the first cable C1 is wound around the outer periphery of the first idler pulley P1x. FIG. 10 shows an example configuration of the first idler pulley P1x including the switching unit. In the example shown in FIG. 10, the switching unit includes a first boss 1001 and a second boss 1002 that protrude so as to provide different winding positions in the first axis direction. The first cable C1 switches the winding positions in the first axis direction by passing through between the first boss 1001 and the second boss 1002. As a result, the winding positions are made different between when the first cable C1 is wound around the first idler pulley P1x and when the first cable C1 is separated from the first idler pulley P1x, so that the cables do not overlap each other.

Also, in the example shown in FIGS. 8 and 9, the second cable C2 attached to the second jaw capstan JC2 is pulled in a direction orthogonal to the second axis. However, as the second cable C2 is wound at least once around a second idler pulley P2x that uses the first axis as its rotation axis, the second cable C2 is inserted through the shaft 102 and is switched to the direction so as to be pulled in the longitudinal axis direction of the shaft 102, and is then wound around the second motor capstan MC2 at the other end. The second cable C2 is wound from the direction in which the distance to the second idler pulley P2x is shortest. Further, when the second motor capstan MC2 is rotated by the second motor M2 to generate the tractive force for the second cable C2, torque about the second axis is applied to the second jaw member J2, so that the second jaw member J2 can be turned in a direction to approach the first jaw member J1 (the closing direction).

Note that a switching unit that switches the winding position in the first axis direction is disposed at a portion on the outer periphery of the second idler pulley P2x so that the cables do not overlap each other when the second cable C2 is wound around the outer periphery of the second idler pulley P2x. The switching unit may have a configuration similar to that shown in FIG. 10.

In the example configuration shown in FIGS. 8 and 9, the idler pulleys for the first cable C1 and the second cable C2 can be made smaller and contribute to making the diameter of the shaft 102 smaller, compared with those in the example configuration shown in FIGS. 3 and 4.

Regardless of whether the idler pulleys for switching the orientations of the first cable C1 and the second cable C2 yet to be inserted through the shaft 102 (or at a portion near the first axis) have configurations shown in FIGS. 3 and 4, or in FIGS. 8 and 9, the first cable C1 is switched to another direction via an idler pulley P1c and is wound around the first motor capstan MC1 at the end portion, after passing through the shaft 102, as shown in FIG. 5. Likewise, after passing through the shaft 102, the second cable C2 is switched to another direction via an idler pulley P2c, and is wound around the second motor capstan MC2 at the end. However, in FIGS. 4 and 9, the idler pulleys P1c and P2c are not shown for convenience sake.

Further, as shown in FIGS. 2 and 5, the first cable C1 and the second cable C2 are wound around the first motor capstan MC1 and the second motor capstan MC2, respectively, and are then connected via a tension spring TS1. Thus, the pre-tension generated from the restoring force of the tension spring TS1 is applied to the first cable C1 and the second cable C2.

Figure 11:
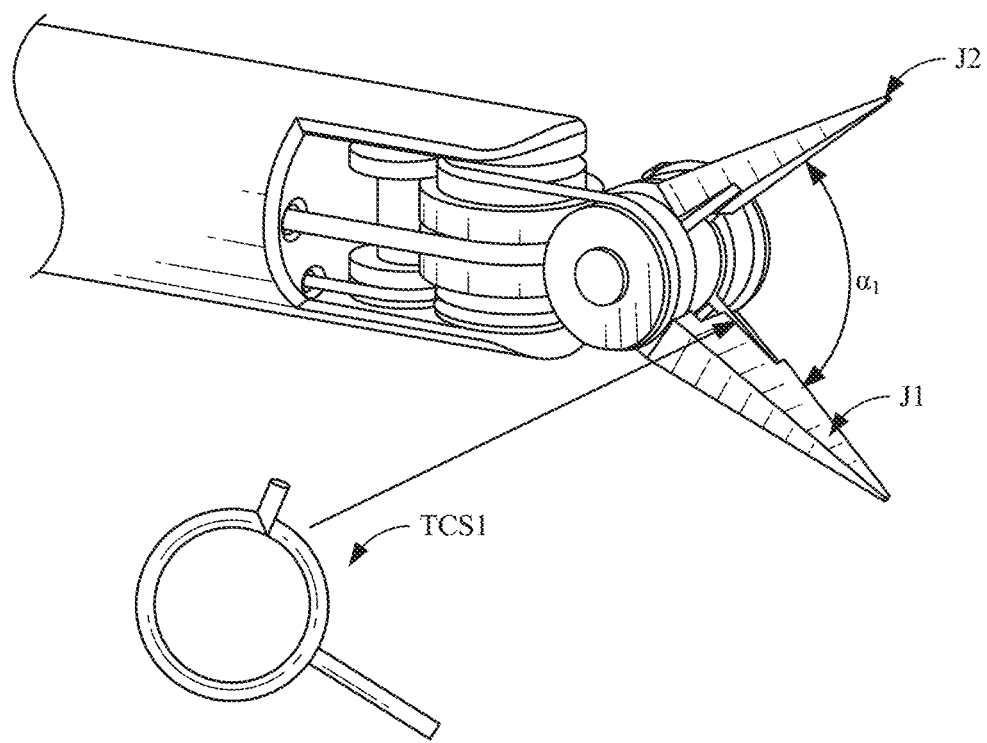
FIG. 11 is a diagram showing an open/closed state (without pre-tension) of a first jaw member J1 and a second jaw member J2.
Figure 12:
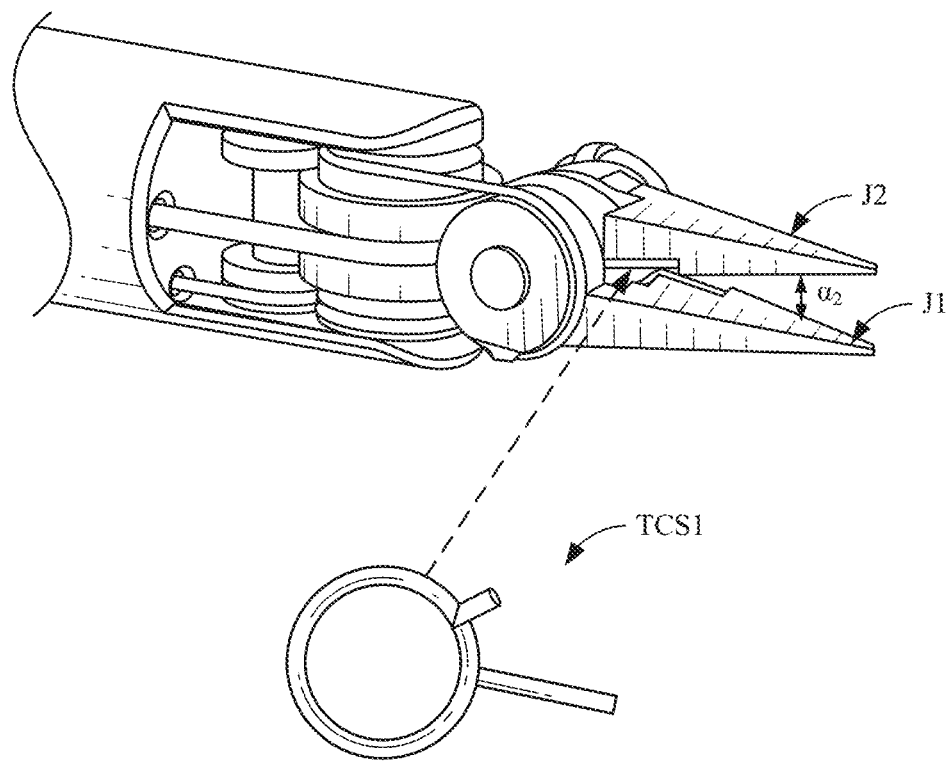
FIG. 12 is a diagram showing an open/closed state (with pre-tension) of the first jaw member J1 and the second jaw member J2.

Here, the pre-tension necessary for the first cable C1 and the second cable C2 is discussed. FIG. 11 shows an open-close state of the first jaw member J1 and the second jaw member J2 before pre-tension is applied to the first cable C1 and the second cable C2. Further, FIG. 12 shows an open-close state of the first jaw member J1 and the second jaw member J2 when pre-tension is applied to the first cable C1 and the second cable C2. Each of the drawings also shows a state in which the first torsion coil spring TCS1 and the second torsion coil spring TCS2 are twisted about the central axis.

The spring constants of first torsion coil spring TCS1 and the second torsion coil spring TCS2 are both represented by $k_{j12}$ [N·mm/deg], and the radii of the first jaw capstan JC1 and the second jaw capstan JC2 are both represented by $R_{j12}$ [mm]. Further, where the open angle of the first cable C1 and the second cable C2 before pre-tension is applied is represented by a1, and the open angle of the first cable C1 and the second cable C2 when pre-tension is applied is represented by $\alpha_2$, the pre-tension $T_{pre\text{-}tension}$ is expressed as in Equation (1) shown below.

[Mathematical Formula 1]

$$T_{pre\text{-}tension} = 2k_{j12} \cdot (\alpha_1 - \alpha_2)/R_{j12}[N] \qquad (1)$$

Therefore, it is preferable to install the tension spring TS1 between the cable C1' and the cable C2' so that the pre-tension $T_p$re-tension is generated for the first cable C1 and the second cable C2.

C. Operations of a Surgical Tool Unit

Next, a specific operation method for the surgical tool unit end portion 101 is described.

Operation at the First Axis:

The third cable including the forward cable C3a and the backward cable C3b is wound in a loop around the third motor capstan MC3 and the wrist capstan WC. Accordingly, when the third motor capstan MC3 is rotated by the third motor M3, a tractive force is generated in the third cable, and the wrist capstan WC can be rotated about the first axis. As a result, the wrist element WE and the end effector mounted on the wrist element WE can be rotated about the first axis.

Operation at the Second Axis:

The average value of the angle of the first jaw member J1 about the second axis and the angle of the second jaw member J2 about the second axis is defined as the angle of the end effector about the second axis. When the first jaw capstan JC1 and the second jaw capstan JC2 rotate in the same direction and at the same speed, a turning operation of the end effector about the second axis is caused.

Operation of the End Effector:

The end effector is formed with a pair of opposing jaw members: the first jaw member J1 and the second jaw member J2 (see FIG. 3, for example). The open angle of the first jaw member J1 and the second jaw member J2 is set as the open-close angle of the end effector. When the first motor capstan MC1 and the second motor capstan MC2 are rotated in opposite directions at the same speed, an opening and closing operation of the end effector is caused.

Figure 13:
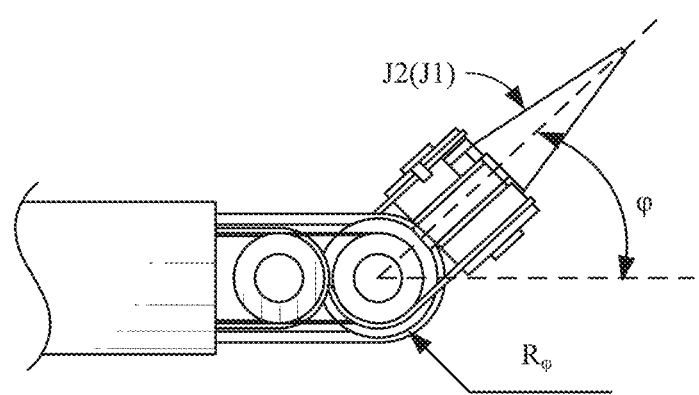
FIG. 13 is a diagram showing an example operation of the wrist element WE turning about the first axis.

FIG. 13 shows an example operation of the wrist element WE about the first axis. Here, the drawing is a view of the surgical tool unit end portion 101 as viewed from a direction parallel to the first axis. As shown in the drawing, the pulley radius of the wrist capstan WC is represented by $R_\psi$, and the turning angle of the wrist element WE about around the first axis is represented by $\psi$.

Figure 14:
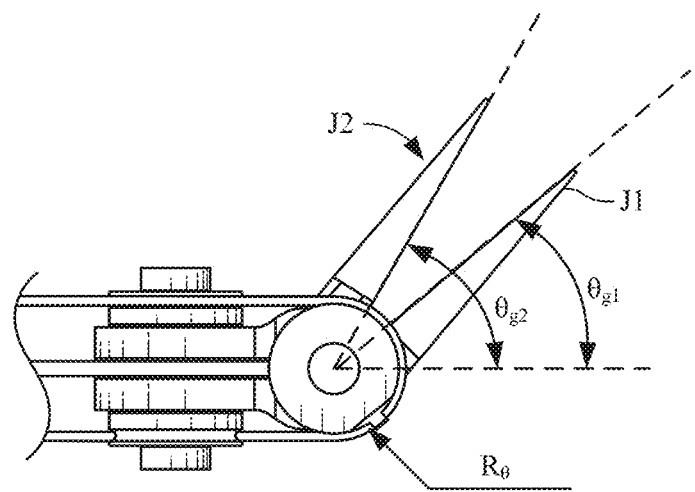
FIG. 14 is a diagram showing an example operation of an end effector turning about the second axis.
Figure 15:
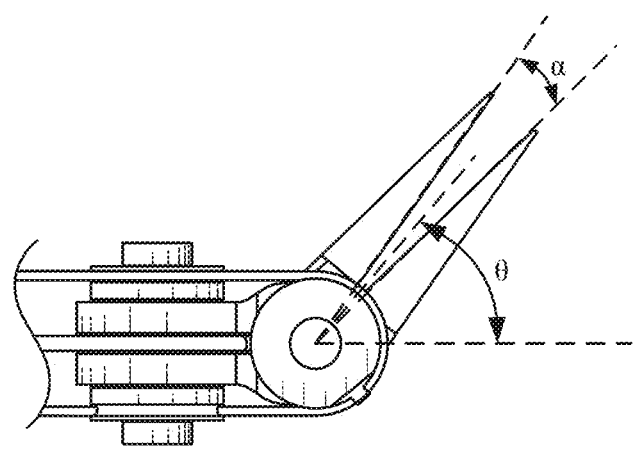
FIG. 15 is a diagram showing an example operation of an end effector turning about the second axis.

Further, FIGS. 14 and 15 show an example operation of the end effector about the second axis. Here, each of the drawings is a view of the surgical tool unit end portion 101 as viewed from a direction parallel to the second axis. As shown in each of the drawings, the pulley radii of the first jaw capstan JC1 and the second jaw capstan JC2 are both represented by $R_\theta$, the turning angle of the first jaw member J1 about the second axis is $\theta_{g1}$, the turning angle of the second jaw member J2 about the second axis is $\theta_{g2}$, the open angle of the end effector is $\alpha$, and the turning angle of the end effector about the second axis is $\theta$.

Further, although not shown in the drawings, the pulley radii of the first motor capstan MC1 and the second motor capstan MC2 are both represented by $R_{m12}$, the pulley radius of the third motor capstan MC3 is $R_{m3}$, the rotation angle of the first motor M1 is $\varphi_{m1}$, the rotation angle of the second motor M2 is $\varphi_{m2}$, and the rotation angle of the third motor M3 is $\varphi_{m3}$.

Here, the turning angle $\psi$ of the wrist element WE about the first axis, the turning angle $\theta$ of the end effector about the second axis, and the open angle $\alpha$ of the end effector are expressed as in the following Equations (2) to (4), respectively.

[Mathematical Formula 2]

$$\psi = \frac{R_{m3}}{R_\psi} \phi_{m3} \qquad (2)$$

[Mathematical Formula 3]

$$\theta = \frac{\theta_{g1} + \theta_{g2}}{2} \qquad (3)$$

[Mathematical Formula 4]

$$\alpha = \theta_{g1} - \theta_{g2} \qquad (4)$$

Meanwhile, the turning angle $\theta_{g1}$ of the first jaw member J1 about the second axis, and the turning angle $\theta_{g2}$ of the second jaw member J2 about the second axis are expressed as in the following Equations (5) and (6), respectively.

[Mathematical Formula 5]

$$\theta_{g2} = \frac{R_{m12}}{R_\theta} \phi_{m2} + \frac{R_\psi}{R_\theta} \psi \qquad (5)$$

[Mathematical Formula 6]

$$\theta_{g1} = -\frac{R_{m12}}{R_\theta} \phi_{m1} + \frac{R_\psi}{R_\theta} \psi \qquad (6)$$

As can be seen from the above Equations (2) to (6), the turning angles $\theta_{g1}$ and $\theta_{g12}$ of the first jaw member J1 and the second jaw member J2 about the second axis do not affect the turning angle $\psi$ of the wrist element WE about the first axis. On the other hand, the turning angle $\psi$ of the wrist element WE about the first axis affects the turning angles $\theta_{g1}$ and $\theta_{g12}$ of the first jaw member J1 and the second jaw member J2 about the second axis. Accordingly, by performing control so as to compensate for the influence of the turning angle $\psi$ of the wrist element WE about the first axis, it is possible to obtain a desired turning angle $\theta$ and open angle $\alpha$ of the target end effector about the second axis.

In short, by controlling the rotation angle $\varphi_{m3}$ of the third motor M3, it is possible to control the turning motion of the wrist element WE about the first axis. Further, by controlling the respective rotation angles $\varphi_{m1}$, $\varphi_{m2}$, and $\varphi_{m3}$ of the first motor M1, the second motor M2, and the third motor M3, it is possible to control the turning motion and the opening and closing motion of the end effector about the second axis.

D. Range of Movement of a Surgical Tool Unit

Next, the range of movement of the surgical tool unit end portion 101 is described.

FIGS. 16 to 21 illustrate examples of opening and closing of the end effector and turning motions about the second axis.

Figure 16:
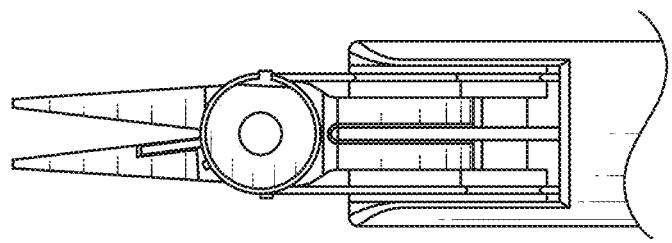
FIG. 16 is a diagram showing an example of opening and closing of the end effector and a turning motion about the second axis.
Figure 17:
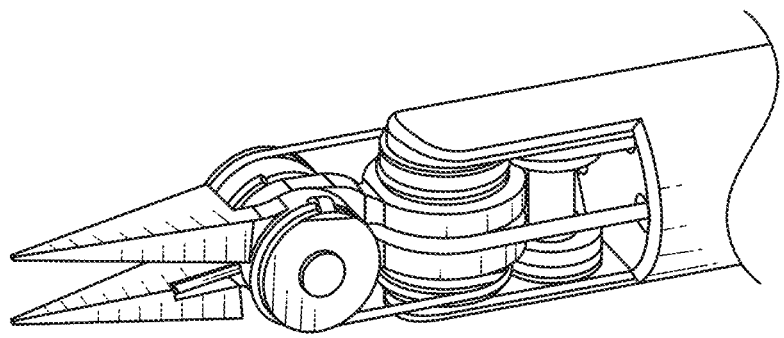
FIG. 17 is a diagram showing an example of opening and closing of the end effector and a turning motion about the second axis.

FIGS. 16 and 17 show a state in which the end effector is opened at the turning angle $\theta=0$ degrees about the second axis. Here, FIG. 16 shows the surgical tool unit end portion 101 as viewed from a direction parallel to the second axis, and FIG. 17 shows the surgical tool unit end portion 101 as viewed from an oblique direction.

Figure 18:
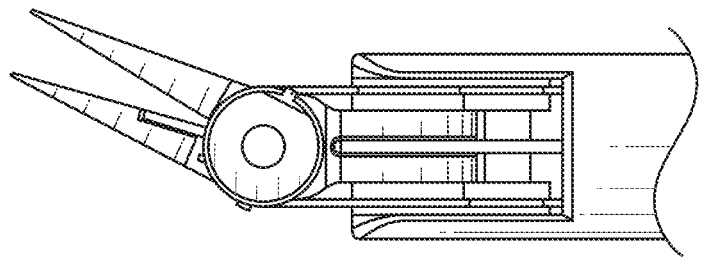
FIG. 18 is a diagram showing an example of opening and closing of the end effector and a turning motion about the second axis.
Figure 19:
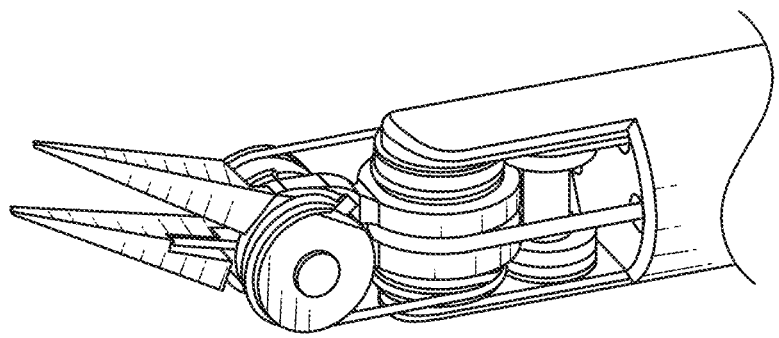
FIG. 19 is a diagram showing an example of opening and closing of the end effector and a turning motion about the second axis.

Further, FIGS. 18 and 19 show a state in which the end effector is opened at the turning angle $\theta=30$ degrees about the second axis. Here, FIG. 18 shows the surgical tool unit end portion 101 as viewed from a direction parallel to the second axis, and FIG. 19 shows the surgical tool unit end portion 101 as viewed from an oblique direction.

Figure 20:
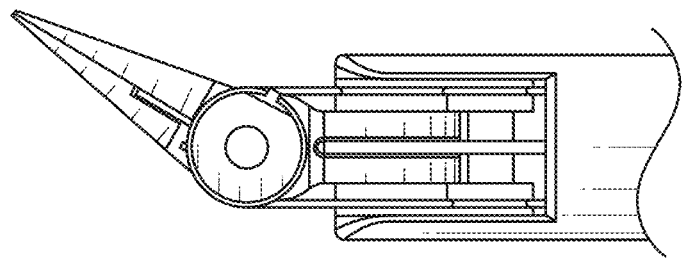
FIG. 20 is a diagram showing an example of opening and closing of the end effector and a turning motion about the second axis.
Figure 21:
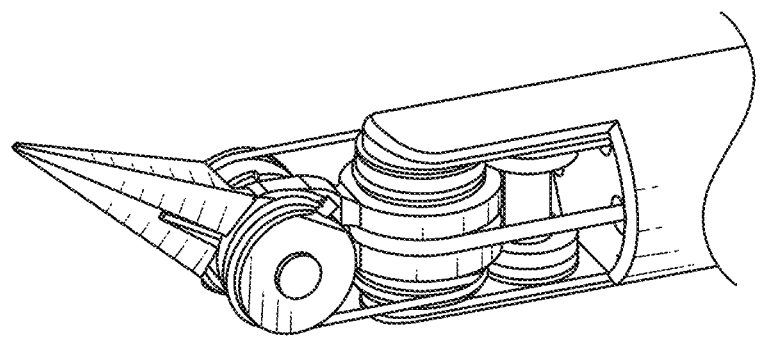
FIG. 21 is a diagram showing an example of opening and closing of the end effector and a turning motion about the second axis.

Further, FIGS. 20 and 21 show a state in which the end effector is closed at the turning angle $\theta=30$ degrees about the second axis. Here, FIG. 20 shows the surgical tool unit end portion 101 as viewed from a direction parallel to the second axis, and FIG. 21 shows the surgical tool unit end portion 101 as viewed from an oblique direction.

FIGS. 22 to 25 illustrate examples of turning motions of the wrist element WE about the first axis, and turning motions of the end effector about the second axis. Here, in any of FIGS. 22 to 25, the end effector is in an open state.

Figure 22:
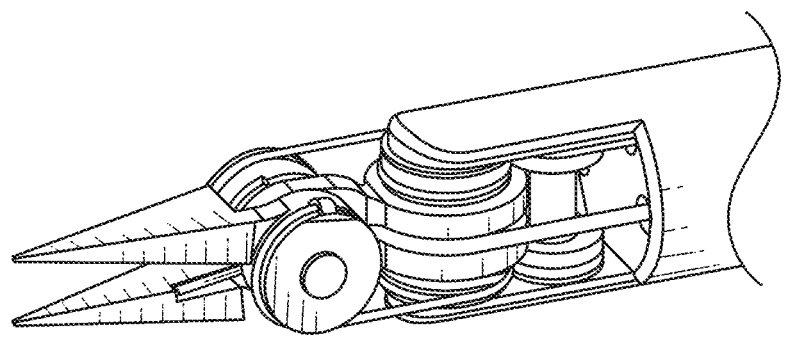
FIG. 22 is a diagram showing an example of a turning motion of the wrist element WE about the first axis, and a turning motion of the end effector about the second axis.
Figure 23:
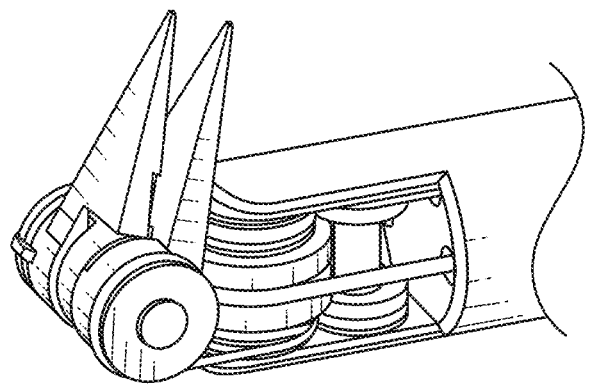
FIG. 23 is a diagram showing an example of a turning motion of the wrist element WE about the first axis, and a turning motion of the end effector about the second axis.
Figure 24:
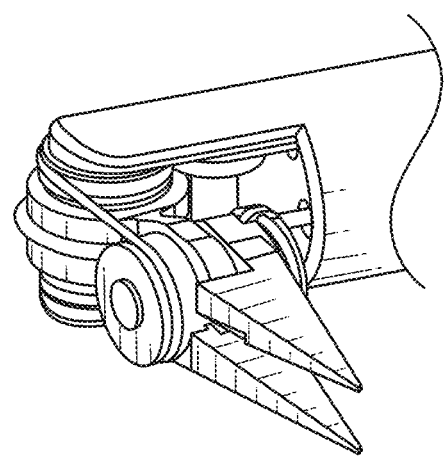
FIG. 24 is a diagram showing an example of a turning motion of the wrist element WE about the first axis, and a turning motion of the end effector about the second axis.
Figure 25:
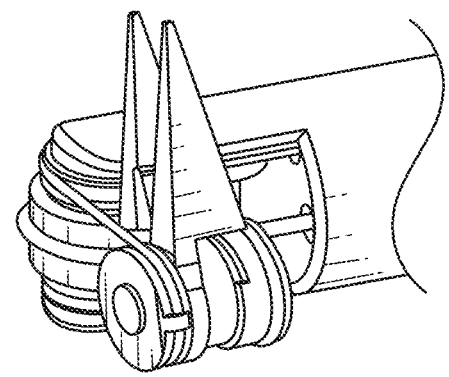
FIG. 25 is a diagram showing an example of a turning motion of the wrist element WE about the first axis, and a turning motion of the end effector about the second axis.

FIG. 22 shows a state in which the turning angle $\psi$ of the wrist element WE about the first axis is 0 degrees, and the turning angle $\theta$ of the end effector about the second axis is 0 degrees. Further, FIG. 23 shows a state in which the turning angle $\psi$ of the wrist element WE about the first axis is 0 degrees, and the turning angle $\theta$ of the end effector about the second axis is 100 degrees. Also, FIG. 24 shows a state in which the turning angle ψ of the wrist element WE about the first axis is 90 degrees, and the turning angle θ of the end effector about the second axis is 0 degrees. Further, FIG. 25 shows a state in which the turning angle ψ of the wrist element WE about the first axis is 90 degrees, and the turning angle θ of the end effector about the second axis is 100 degrees.

The cables for pulling the first jaw capstan JC1 and the second jaw capstan JC2 are only required to be the single first cable C1 and the single second cable C2, respectively. The portion at which the first cable C1 is joined to the first jaw capstan JC1 can be located at the point where the first cable C1 is wound 90 degrees or greater around the outer periphery of the first jaw capstan JC1. The portion at which the second cable C2 is joined to the second jaw capstan JC2 can also be located at the point of winding 90 degrees or greater.

To maintain a wider range of movement of the end effector about the second axis, it is preferable to provide a portion at which the first cable C1 and the second cable C2 joined to the first jaw capstan JC1 and the second jaw capstan JC2, respectively, at the positions where each of the cables is wound 150 degrees, while the turning angle ψ of the wrist element WE about the first axis is 0 degrees, and the turning angle θ of the end effector about the second axis is 0 degrees. With this arrangement, a movement range of ±90 degrees or greater about the second axis can be secured for the end effector.

E. Modifications of the Surgical Tool Unit

E-1. Modifications of the Method for Applying Repulsive Force Between the Jaw Members Instead of torsion coil springs (see FIGS. 6 and 7), a helical compression spring may be used for the spring SP that constantly applies a repulsive force between the first jaw member J1 and the second jaw member J2.

FIGS. 26 to 31 show an example configuration of the surgical tool unit end portion 101 that generates a repulsive force between the first jaw member J1 and the second jaw member J2 using a helical compression spring, and also show motions of the end effector opening/closing and turning about the second axis.

Figure 26:
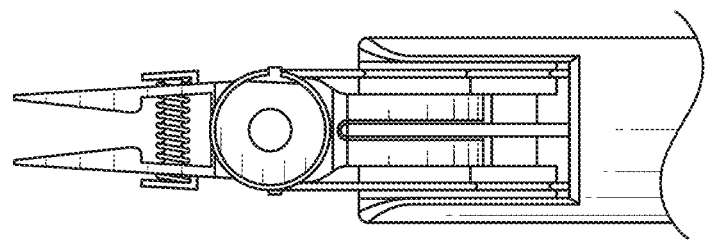
FIG. 26 is a diagram showing a modification of the surgical tool unit end portion 101 (an example configuration for applying a repulsive force between the jaw members using a helical compression spring).
Figure 27:
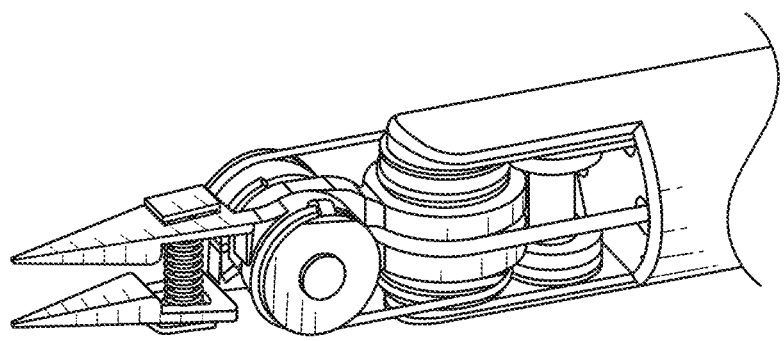
FIG. 27 is a diagram showing a modification of the surgical tool unit end portion 101 (an example configuration for applying a repulsive force between the jaw members using a helical compression spring).
Figure 28:
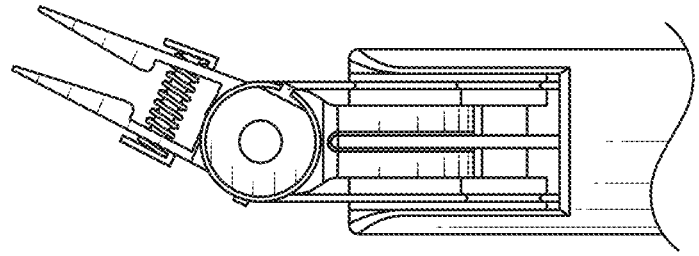
FIG. 28 is a diagram showing a modification of the surgical tool unit end portion 101 (an example configuration for applying a repulsive force between the jaw members using a helical compression spring).
Figure 29:
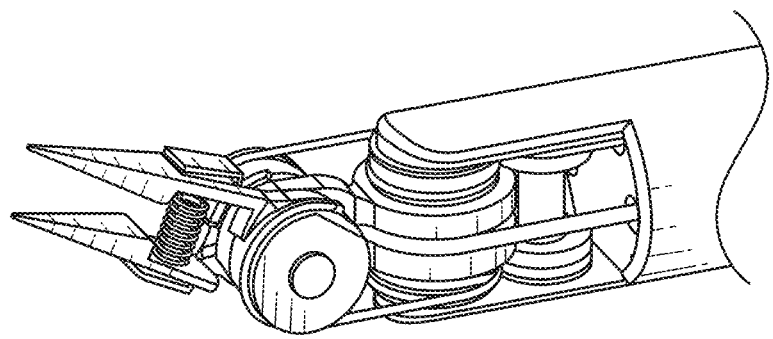
FIG. 29 is a diagram showing a modification of the surgical tool unit end portion 101 (an example configuration for applying a repulsive force between the jaw members using a helical compression spring).

FIGS. 26 and 27 show a state in which the end effector is opened at the turning angle θ=0 degrees about the second axis. Also, FIGS. 28 and 29 show a state in which the end effector is opened at the turning angle θ=30 degrees about the second axis. Further, FIGS. 30 and 31 show a state in which the end effector is closed at the turning angle θ=30 degrees about the second axis.

Figure 30:
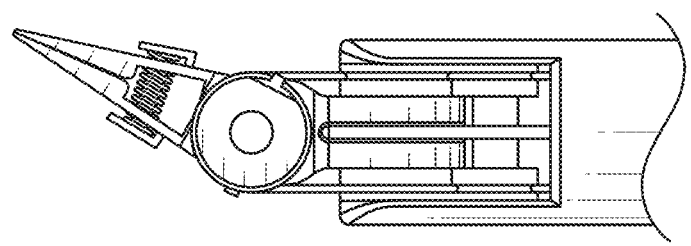
FIG. 30 is a diagram showing a modification of the surgical tool unit end portion 101 (an example configuration for applying a repulsive force between the jaw members using a helical compression spring).
Figure 31:
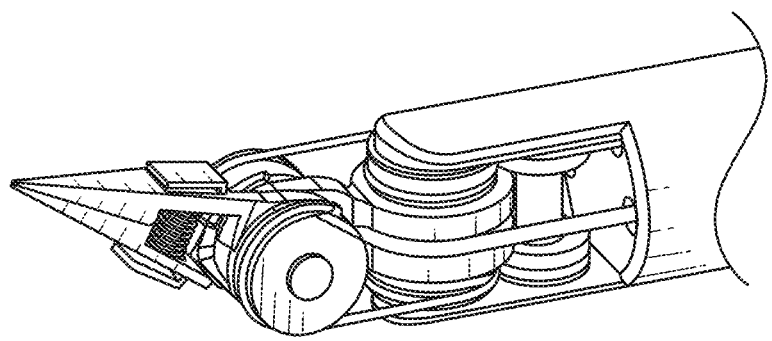
FIG. 31 is a diagram showing a modification of the surgical tool unit end portion 101 (an example configuration for applying a repulsive force between the jaw members using a helical compression spring).

Here, FIGS. 26, 28, and 30 show the surgical tool unit end portion 101 as viewed from a direction parallel to the second axis, and FIGS. 27, 29, and 31 show the surgical tool unit end portion 101 as viewed from an oblique direction.

Note that the spring SP can be replaced with some other elastic member or a repulsive force generating device that is capable of applying a certain repulsive force between the jaw members, regardless of the posture of the surgical tool. For example, the substitute may be a polymeric elastic member, a bellows pressurized by air, or a tension spring attached so as to apply a repulsive force between the jaw members.

Alternatively, the first jaw member J1 and the second jaw member J2 may be integrally molded like tweezers formed with a metal rod folded in two, to obtain a structure having an elastic force in the opening direction.

E-2. Modifications of the Method for Driving the Cables

In the examples described above, rotary motors are used as the actuators for pulling the cables. Linear actuators can also be used as the actuators for pulling the cables.

Figure 32:
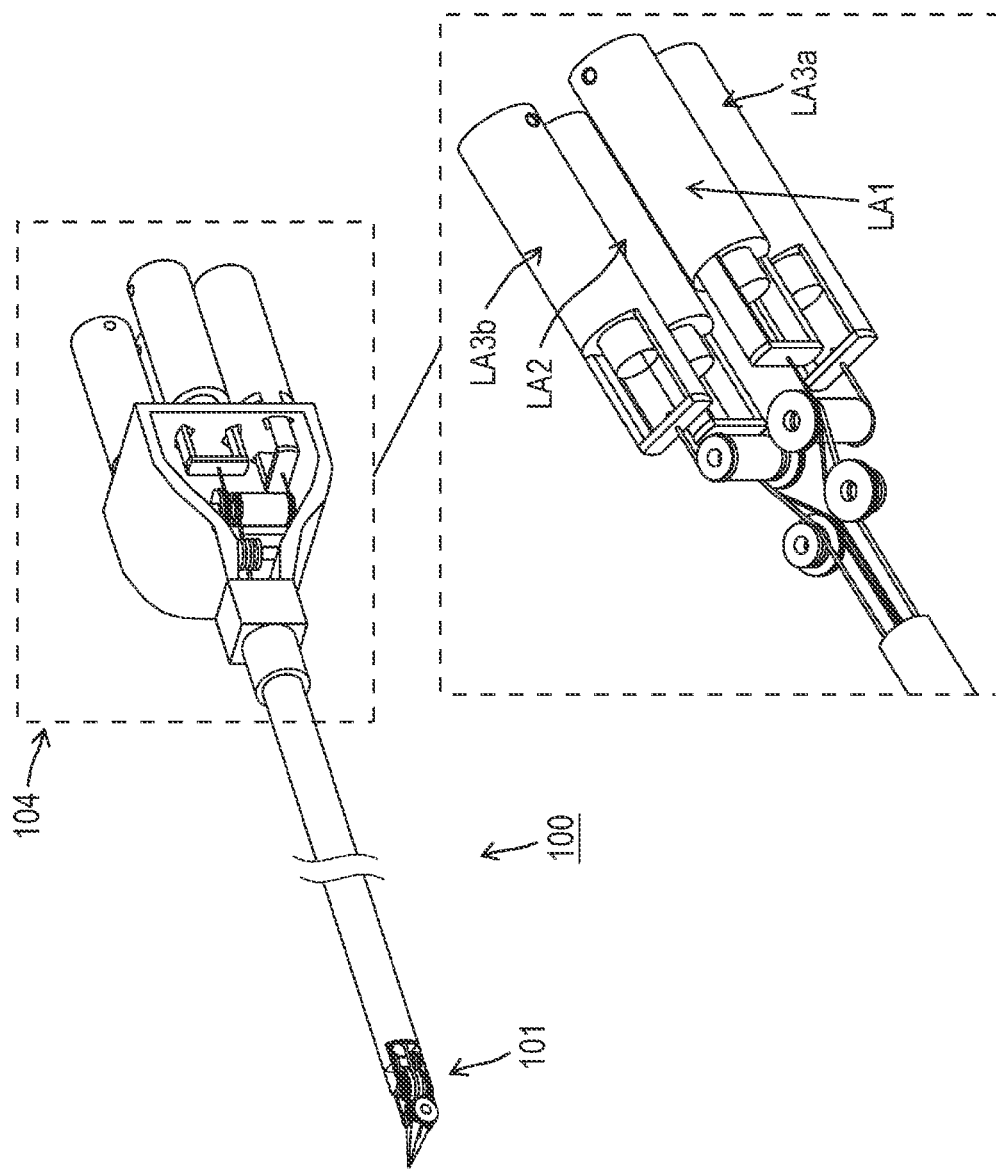
FIG. 32 is a diagram showing a modification of a surgical tool unit (an example configuration using linear actuators for pulling the cables).

FIG. 32 shows an example configuration of a surgical tool unit that is designed to pull the first cable C1, the second cable C2, and the forward cable C3a and the backward cable C3b of the third cable, with linear actuators LA1, LA2, LA3a, and LA3b, respectively. In the drawing, an enlarged view of the surgical tool unit drive unit 103 is also shown.

Pneumatic actuators can be used as the linear actuators LA1, LA2, LA3a, and LA3b. Further, examples of other modifications of the actuators that pull the cables may include the following.

Piezoelectric linear-motion ultrasonic motors
Piezoelectric rotary ultrasonic motors
Hydraulic linear motors
Hydraulic rotary motors
Polymeric linear actuators
Electromagnetic linear motors
Shape-memory alloys Further, regardless of which kind of actuator is adopted, the actuators may be equipped with a speed reducer, a position detector, and an emergency brake mechanism. Here, examples of the speed reducers include gear reducers, wave gear reducers, planetary gear reducers, paradox planetary gear reducers, cable reducers, traction reducers, ball screws, sliding screws, and worm gears. Further, examples of the position detectors include magnetic encoders, optical encoders, and potentiometers.

E-3. Modifications of the Shape of the Jaw Members

In each of the drawings, the first jaw member J1 and the second jaw member J2 are drawn in simple shapes for convenience sake. In practice, the shape of the jaw members may be changed depending on the purpose of use of the surgical tool unit. For example, the following forms can be adopted.

Forceps
Bipolar forceps
Scissors
Staplers

E-4. Modifications of the Shaft

The shaft 102 is ideally a rigid body, but may have a flexible configuration. Further, in each drawing, the shaft 102 having a simple hollow cylindrical shape is shown for simplification. However, the shaft does not necessarily have a cylindrical shape. For example, a cross-section of the shaft 102 may have a polygonal shape or an elliptical shape, or its cross-sectional shape may change midway in the longitudinal axis direction.

E-5. Modifications of the Cables

A cable may be a bundle of metallic wires, a bundle of resin, or a mixture of a plurality of materials such as metal wires and resin. Also, a shaft 102 formed with a metal having a high rigidity may be used at a cable portion that is disposed inside the shaft 102 or the like and does not need to be curved, and be connected to a flexible cable that is used at a portion having a curve. In this manner, one cable may be formed. Examples of substitutes for the cables include the following.

Metallic or resin wires
Wires obtained by weaving thin metallic or resin wires having a small diameter E-6. Modifications of the Idler Pulleys In the examples described above, idler pulleys are used for adjusting the layout of the cables. With the use of idler pulleys, the sliding friction at a time when the cables are pulled can be reduced, and a smooth operation can be performed. In a case where sliding friction is to be reduced, idler pulleys each having a rotational bearing may be used. However, the use of idler pulleys adds to the size of the mechanism, and the number of components becomes larger. Therefore, to further reduce the size of the surgical tool unit end portion 101, cables may be laid out along guide grooves formed in the mechanism without any idler pulley.

E-7. Sensing

To detect the tension of the cables, a strain sensor may be mounted on each cable. Examples of the strain sensor include a variable-resistance strain sensor and a fiber Bragg grating (FBG) strain sensor. Alternatively, a torque sensor may be mounted on the actuators that pull cables.

F. Example Applications of the Surgical Tool Unit

F-1. Example Application to a Surgery Support System

Figure 33:
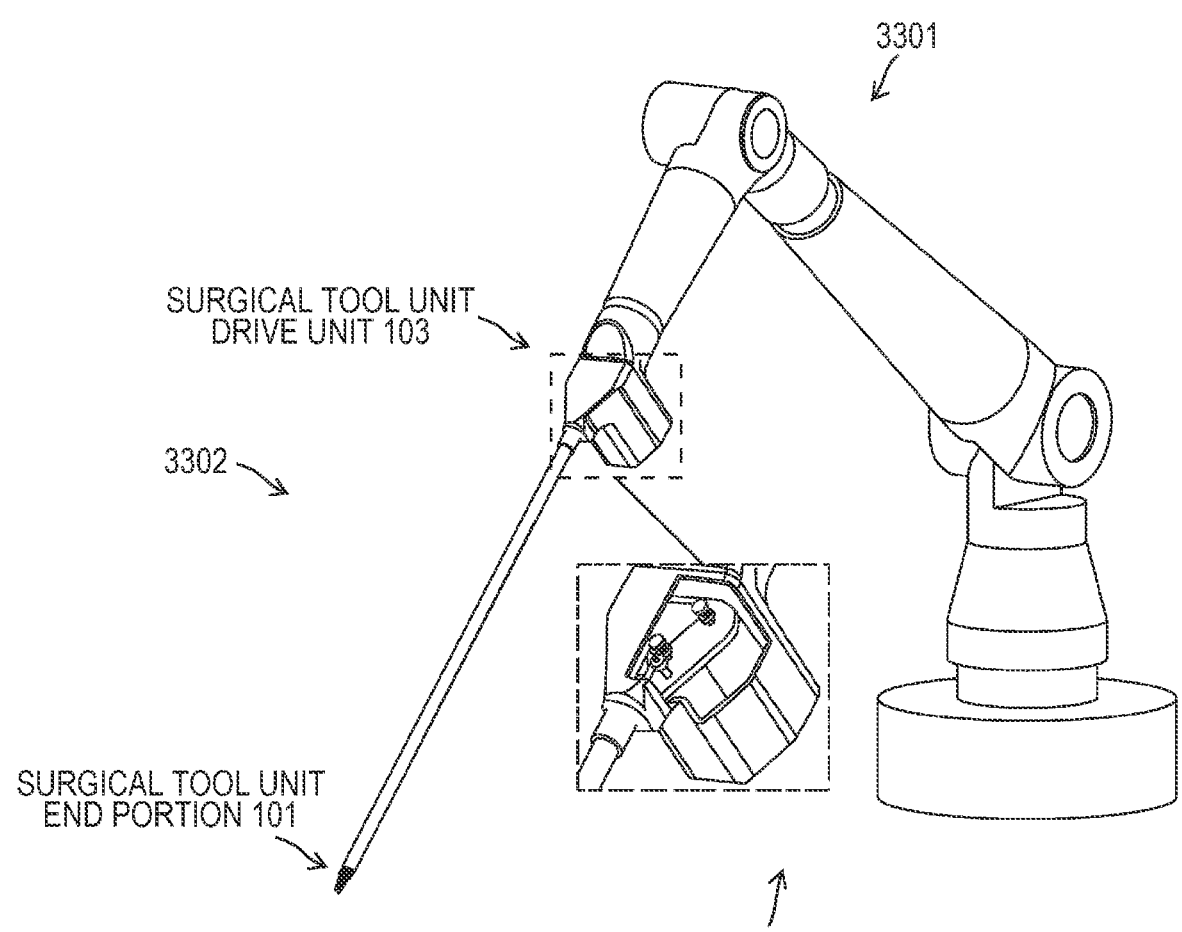
FIG. 33 is a diagram showing an example external configuration of a surgery support system 3300.

FIG. 33 shows an example external configuration of a surgery support system 3300 using a surgical tool unit according to this embodiment. The surgery support system 3300 shown in the drawing includes an arm 3301 having a multi-link structure, and a surgical tool unit 3302 is attached to the end of the arm 3301. The surgical tool unit 3302 may be replaceable. The surgery support system 3300 is used in laparoscopic surgery, for example, and the surgical tool unit end portion 101 is inserted into an abdominal cavity through a trocar (not shown), to perform an operation such as gripping and cutting of an affected part.

The surgery support system 3300 shown in the drawing is used as the slave device in a master-slave robot, for example, and the arm 3301 and the surgical tool unit 3302 are driven in accordance with an instruction from the master device (not shown). Further, a bilateral control method is applied to this type of master-slave robot, for example.

Note that the arm 3301 may be a robot of any mechanism type such as a polar-coordinate robot, a cylindrical coordinate robot, a Cartesian coordinate robot, a vertical articulated robot, a horizontal articulated robot, a parallel link robot, or a remote center of motion (RCM) robot.

Further, in a case where the surgery support system 3300 is a surgical robot that supports laparoscopic surgery, the arm 3301 is preferably a vertical articulated arm or a remote center of motion (RCM) arm that has its remote rotation center at a position away from the driving rotation center and performs a pivoting (fixed-point) motion, so as to achieve compactness of the mechanism, ease of a pivoting motion generation at the site of a trocar, and the like.

Furthermore, although FIG. 33 shows an example configuration of a surgery support system to which only one surgical tool unit can be attached, the present technology can also be applied to a surgery support system of a type to which a plurality of surgical tool units can be simultaneously attached to perform laparoscopic surgery.

F-2. Example Application to a Surgical Operating Unit

Figure 34:
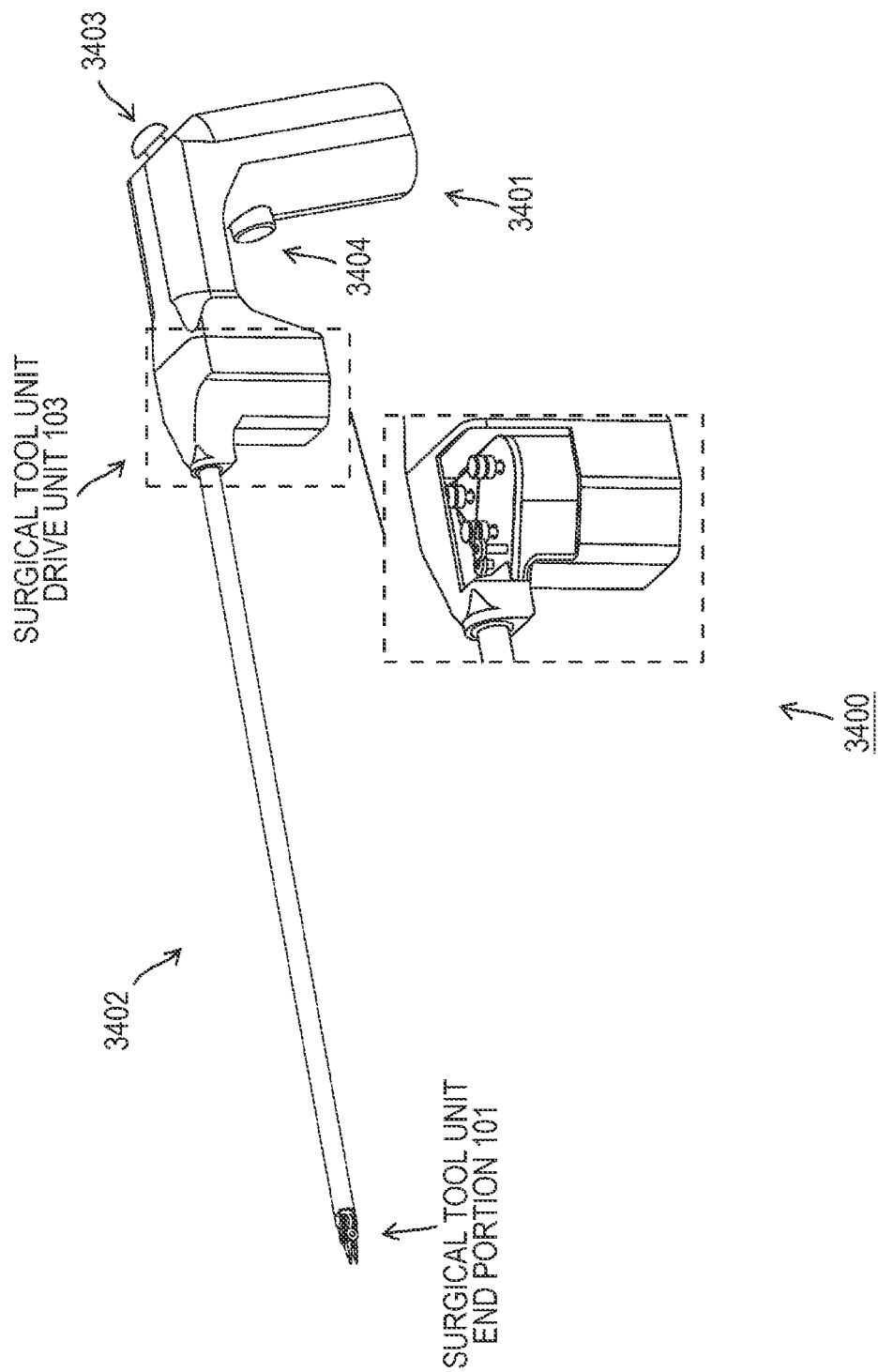
FIG. 34 is a diagram showing an example external configuration of a surgical operating unit 3400.

FIG. 34 shows an example external configuration of a surgical operating unit 3400 using a surgical tool unit according to this embodiment. The surgical operating unit 3400 includes a handle unit 3401 that is directly held and operated by a user (operator) by hand, and a surgical tool unit 3402 is attached to the end of the handle unit 3401. The surgical tool unit 3402 may be replaceable.

The handle unit 3401 may include a joystick 3403 that can be handled with a thumb to designate a desired orientation of the posture of the surgical tool unit end portion of the surgical tool unit 3402, for example. The handle unit 3401 may also include a button 3404 that can be pushed with an index finger to issue an instruction for an opening and closing operation of the jaw members.

A controller (not shown) is installed in the handle unit 3401. The controller calculates the turning angle of the wrist element WE about the first axis, and the turning angle and the open angle of the end effector about the second axis, in accordance with the amount of operation of the joystick 3403 or the button 3404. The controller then converts these angles into the amount of rotation of each motor, and outputs a control signal to the surgical tool unit drive unit 103.

G. Effects

By the technology according to the present disclosure, a turning motion (about the second axis) of an end effector including a pair of opposing jaw members, and an opening and closing motion of the jaw members can be caused with two cables. Accordingly, the number of idler pulleys to be used for pulling the cables can be reduced, and the diameter of the end portion of the surgical tool unit can be easily made smaller. In particular, the number of idler pulleys to be disposed in series on the turning axis (the first axis) of the end effector is two, and thus, a smaller diameter is easily achieved.

Also, by the technology according to the present disclosure, the number of cables and the number of idler pulleys to be used in a surgical tool unit are small, which is advantageous in cost reduction. Since the number of components is small as described above, the structure of a surgical tool unit is simplified. Thus, the assembly cost can be lowered, and maintenance is facilitated.

Further, by the technology according to the present disclosure, each jaw member is pulled by one cable. However, the joining portion between a jaw capstan and a cable can be set at any desired position on the jaw capstan. Thus, the range of movement of each jaw member can be made wider.

Furthermore, in a surgical tool unit to which the technology according to the present disclosure is applied, the wrist element, and the end effector that is mounted on the wrist element and is equipped with an opening and closing mechanism can be driven with three motors, and the number of cables is small. Accordingly, the layout of the cables in the surgical tool unit drive unit can be simplified. Thus, the surgical tool unit can be made compact in size and light in weight.

Also, in a surgical tool unit to which the technology according to the present disclosure is applied, any idler pulley is not disposed on the wrist element. Thus, the distance from the first axis to the second axis can be made shorter.

INDUSTRIAL APPLICABILITY

The technology according to the present disclosure has been described in detail so far, with reference to specific embodiments. However, it is obvious that those skilled in the art can make modifications to and substitutions of the embodiments without departing from the scope of the technology according to the present disclosure.

In this specification, embodiments in which the technology according to the present disclosure is applied to a surgical tool to be used in a surgery support system have been mainly described. However, the subject matter of the technology according to the present disclosure is not limited to these embodiments. The technology according to the present disclosure can be applied to robots in various fields other than medical care, such as precision work robots. The technology according to the present disclosure can also be applied to a grip-type surgical operating unit and a precision work device a user can operate while gripping it with a hand.

In short, the technology according to the present disclosure has been described through examples, and the descriptions in this specification should not be interpreted in a restrictive manner. The claims should be taken into account in understanding the subject matter of the technology according to the present disclosure.

Note that the technology according to the present disclosure may also be embodied in the configurations described below.

(1) A surgical tool including:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

(2) The surgical tool according to (1), in which
the elastic member includes a first elastic member that applies the repulsive force to the first jaw member, and a second elastic member that applies the repulsive force to the second jaw member.

(3) The surgical tool according to (1), further including:
a first jaw capstan that is provided for the first jaw member, and uses the second axis as a rotation axis;
a first cable that is wound around the first jaw capstan;
a second jaw capstan that is provided for the second jaw member, and uses the second axis as a rotation axis; and
a second cable that is wound around the second jaw capstan, in which
the first jaw member turns in a direction toward the second jaw member by pulling the first cable, and the second jaw member turns in a direction toward the first jaw member by pulling the second cable.

(4) The surgical tool according to (3), further including:
a wrist capstan that is provided for the wrist, and uses the first axis as a rotation axis; and
a third cable that includes forward and backward cables wound around the wrist capstan from opposite directions.

(5) The surgical tool according to (4), further including:
a first actuator that pulls the first cable;
a second actuator that pulls the second cable; and
a third actuator that pulls the third cable.

(6) The surgical tool according to any one of (1) to (5), in which
the elastic member has a natural length in which the repulsive force acts even at a maximum open angle of the first jaw member and the second jaw member.

(7) The surgical tool according to any one of (3) to (6), further including:
a first idler pulley unit that switches the first cable to a direction substantially parallel to a longitudinal axis of the shaft; and
a second idler pulley unit that switches the second cable to a direction substantially parallel to the longitudinal axis of the shaft.

(8) The surgical tool according to (7), in which
the first idler pulley unit includes a first idler pulley that rotates about the first axis, and a first adjacent idler pulley that is adjacent to the first idler pulley and has a rotation axis parallel to the first axis, and
the second idler pulley unit includes a second idler pulley that rotates about the first axis, and a second adjacent idler pulley that is adjacent to the second idler pulley and has a rotation axis parallel to the first axis.

(9) The surgical tool according to (7), in which
the first idler pulley unit includes a first idler pulley that rotates about the first axis, the first cable being wound at least once around the first idler pulley, and
the second idler pulley unit includes a second idler pulley that rotates about the first axis, the second cable being wound at least once around the second idler pulley.

(10) The surgical tool according to (9), in which
at least one of the first idler pulley and the second idler pulley includes a switching unit that switches cable winding positions in a first axis direction, to avoid a cable overlap when the first cable is wound.

(11) The surgical tool according to any one of (3) to (10), further including
a pre-tension applying unit that applies pre-tension to the first cable and the second cable.

(12) The surgical tool according to any one of (4) to (11), further including
a pre-tension applying unit that applies pre-tension to the third cable.

(13) The surgical tool according to any one of (4) to (11), in which
a tension difference that is generated between the forward and backward cables by drive of the third actuator applies rotation torque to the wrist capstan, to cause the wrist to rotate about the first axis.

(14) The surgical tool according to any one of (3) to (13), in which,
to cause a change in a difference between angles of the first jaw member and the second jaw member about the second axis, tension of the first cable and the second cable is controlled by drive of the first actuator and the second actuator.

(15) The surgical tool according to any one of (3) to (13), in which,
to cause a change in a sum of angles of the first jaw member and the second jaw member about the second axis, tension of the first cable and the second cable is controlled by drive of the first actuator and the second actuator.

(16) A surgery support system including a surgical tool, and an arm to which the surgical tool is attached,
the surgical tool including:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

(17) A surgical operating unit including a surgical tool, and a handle unit to which the surgical tool is attached,
the surgical tool including:
a shaft;
a wrist that is connected to an end of the shaft rotatably about a first axis;
a first jaw member and a second jaw member, each of which is supported rotatably about a second axis with respect to the wrist; and
an elastic member that applies a repulsive force between the first jaw member and the second jaw member.

REFERENCE SIGNS LIST

100 Surgical tool unit
101 Surgical tool unit end portion

102 Shaft
103 Surgical tool unit drive unit
3300 Surgery support system
3301 Arm
3302 Surgical tool unit
3400 Surgical operating unit
3401 Handle unit
3402 Surgical tool unit
3403 Joystick
3404 Button

The invention claimed is:

1. A surgical tool, comprising:
a shaft;
a wrist rotatably connected to an end of the shaft about a first axis;
a first jaw member and a second jaw member, wherein each of the first jaw member and the second jaw member is rotatably supported about a second axis with respect to the wrist;
a spring configured to apply a repulsive force between the first jaw member and the second jaw member;
a first jaw capstan in contact with the first jaw member, wherein the first jaw capstan is configured to rotate about the second axis;
a first cable wound around the first jaw capstan;
a second jaw capstan in contact with the second jaw member, wherein the second jaw capstan is configured to rotate about the second axis;
a second cable wound around the second jaw capstan;
a wrist capstan for the wrist, wherein the wrist capstan is configured to rotate about the first axis; and
a third cable that includes a forward cable and a backward cable wound around the wrist capstan from opposite directions.

2. The surgical tool according to claim 1, wherein the spring includes:
a first torsion coil spring that is configured to apply the repulsive force to the first jaw member, and
a second torsion coil spring that is configured to apply the repulsive force to the second jaw member.

3. The surgical tool according to claim 1,
wherein
the first jaw member is configured to turn in a direction toward the second jaw member in a case where the first cable is pulled, and
the second jaw member is configured to turn in a direction toward the first jaw member in a case where the second cable is pulled.

4. The surgical tool according to claim 3, further comprising:
a first idler pulley unit configured to switch the first cable to a direction substantially parallel to a longitudinal axis of the shaft; and
a second idler pulley unit configured to switch the second cable to the direction substantially parallel to the longitudinal axis of the shaft.

5. The surgical tool according to claim 4, wherein the first idler pulley unit includes:
a first idler pulley configured to rotate about the first axis, and
a first adjacent idler pulley that is adjacent to the first idler pulley, wherein a rotation axis of the first adjacent idler pulley is parallel to the first axis, and
the second idler pulley unit includes:
a second idler pulley configured to rotate about the first axis, and
a second adjacent idler pulley that is adjacent to the second idler pulley, wherein a rotation axis of the second adjacent idler pulley is parallel to the first axis.

6. The surgical tool according to claim 4, wherein
the first idler pulley unit includes a first idler pulley configured to rotate about the first axis, wherein the first cable is wound at least once around the first idler pulley, and
the second idler pulley unit includes a second idler pulley configured to rotate about the first axis, wherein the second cable is wound at least once around the second idler pulley.

7. The surgical tool according to claim 6, wherein
at least one of the first idler pulley and the second idler pulley includes a switching boss assembly, and
the switching boss assembly is configured to switch cable winding positions in a first axis direction, to avoid a cable overlap in a case where the first cable is wound.

8. The surgical tool according to claim 1, further comprising:
a first actuator configured to pull the first cable;
a second actuator configured to pull the second cable; and
a third actuator configured to pull the third cable.

9. The surgical tool according to claim 8, wherein
the third actuator is configured to be driven,
a tension difference is configured to generate between the forward cable and backward cable based on the drive of the third actuator,
the third actuator is configured to apply rotation torque to the wrist capstan based on the tension difference, and
the wrist is configured to rotate about the first axis based on the applied rotation torque.

10. The surgical tool according to claim 8, wherein
the first actuator and the second actuator are configured to be driven,
tension of the first cable and the second cable is configured to be adjusted based on the drive of the first actuator and the second actuator, and
a change in a difference between angles of the first jaw member and the second jaw member about the second axis is based on the adjusted tension.

11. The surgical tool according to claim 8, wherein
the first actuator and the second actuator are configured to be driven,
a change in a sum of angles of the first jaw member and the second jaw member is about the second axis,
tension of the first cable and the second cable is configured to be adjusted based on the drive of the first actuator and the second actuator, and
the change in the sum of angles of the first jaw member and the second jaw member about the second axis is based on the adjusted tension.

12. The surgical tool according to claim 1, wherein the spring has a natural length in which the repulsive force acts even at a maximum open angle of the first jaw member and the second jaw member.

13. The surgical tool according to claim 1, further comprising a first tension spring configured to apply pre-tension to the first cable and the second cable.

14. The surgical tool according to claim 13, further comprising a second tension spring configured to apply pre-tension to the third cable.

15. A surgery support system, comprising:
a surgical tool; and
an arm to which the surgical tool is attached, wherein the surgical tool includes:

a shaft;

a wrist rotatably connected to an end of the shaft about a first axis;

a first jaw member and a second jaw member, wherein each of the first jaw member and the second jaw member is rotatably supported about a second axis with respect to the wrist;

a spring configured to apply a repulsive force between the first jaw member and the second jaw member;

a first jaw capstan in contact with the first jaw member, wherein the first jaw capstan is configured to rotate about the second axis;

a first cable wound around the first jaw capstan;

a second jaw capstan in contact with the second jaw member, wherein the second jaw capstan is configured to rotate about the second axis;

a second cable wound around the second jaw capstan;

a wrist capstan for the wrist, wherein the wrist capstan is configured to rotate about the first axis; and a third cable that includes a forward cable and a backward cable wound around the wrist capstan from opposite directions.

16. A surgical operating unit, comprising:

a surgical tool; and a handle unit to which the surgical tool is attached, wherein the surgical tool includes:

a shaft;

a wrist rotatably connected to an end of of the shaft about a first axis;

a first jaw member and a second jaw member, wherein each of the first jaw member and the second jaw member is rotatably supported about a second axis with respect to the wrist;

a spring configured to apply a repulsive force between the first jaw member and the second jaw member;

a first jaw capstan in contact with the first jaw member, wherein the first jaw capstan is configured to rotate about the second axis;

a first cable wound around the first jaw capstan;

a second jaw capstan in contact with the second jaw member, wherein the second jaw capstan is configured to rotate about the second axis;

a second cable wound around the second jaw capstan;

a wrist capstan for the wrist, wherein the wrist capstan is configured to rotate about the first axis; and a third cable that includes a forward cable and a backward cable wound around the wrist capstan from opposite directions.

\* \* \* \* \*